US008948850B2

(12) United States Patent
Roth

(10) Patent No.: US 8,948,850 B2
(45) Date of Patent: *Feb. 3, 2015

(54) NON-CONTACT THERMOMETER SENSING A CAROTID ARTERY

(71) Applicant: Jason Roth, Boca Raton, FL (US)

(72) Inventor: Jason Roth, Boca Raton, FL (US)

(73) Assignee: Arc Devices Limited, Belfast (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/889,553

(22) Filed: May 8, 2013

(65) Prior Publication Data
US 2014/0088435 A1    Mar. 27, 2014

Related U.S. Application Data

(63) Continuation of application No. 13/624,874, filed on Sep. 21, 2012, now Pat. No. 8,452,382.

(51) Int. Cl.
A61B 6/00 (2006.01)
A61B 5/00 (2006.01)
A61B 5/01 (2006.01)
G01J 5/02 (2006.01)
G01J 5/08 (2006.01)
G01J 5/00 (2006.01)

(52) U.S. Cl.
CPC ............ *A61B 5/6817* (2013.01); *A61B 5/6887* (2013.01); *A61B 5/01* (2013.01); *G01J 5/025* (2013.01); *G01J 5/0809* (2013.01); *G01J 5/0025* (2013.01); *A61B 5/0086* (2013.01); *A61B 5/0075* (2013.01); *A61B 5/015* (2013.01); *A61B 2562/0233* (2013.01); *A61B 2562/0271* (2013.01)
USPC .......... 600/473; 600/407; 600/474; 600/475; 600/476; 600/309; 600/310

(58) Field of Classification Search
USPC .......................... 600/407, 473–477, 309–310
See application file for complete search history.

(56) References Cited

U.S. PATENT DOCUMENTS

| 4,634,294 | A | * | 1/1987 | Christol et al. | 374/170 |
| 5,150,969 | A | * | 9/1992 | Goldberg et al. | 374/128 |
| 7,340,293 | B2 | * | 3/2008 | McQuilkin | 600/474 |
| 2004/0254472 | A1 | * | 12/2004 | McQuilkin | 600/473 |
| 2007/0055171 | A1 | * | 3/2007 | Fraden | 600/549 |

* cited by examiner

*Primary Examiner* — James Kish
(74) *Attorney, Agent, or Firm* — Michael G. Smith, Esq.

(57) ABSTRACT

Methods and apparatus are provided which in some implementations a non-contact thermometer determines a temperature of a subject from a carotid source point of the subject.

19 Claims, 21 Drawing Sheets

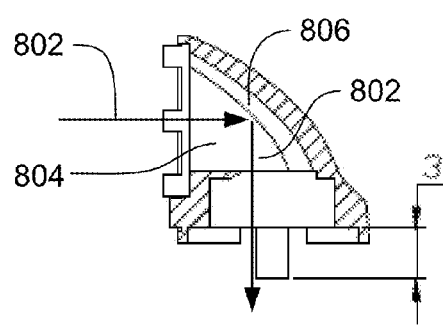
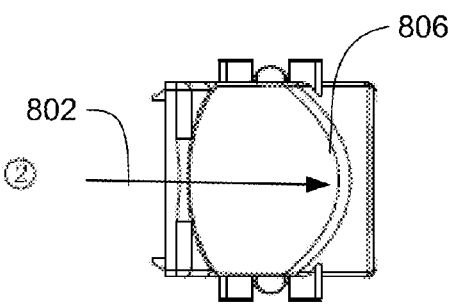
FIG. 8    FIG. 9
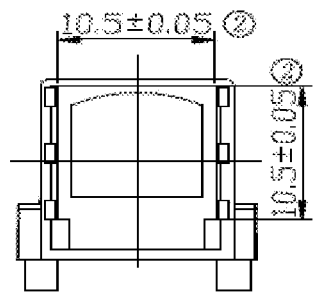
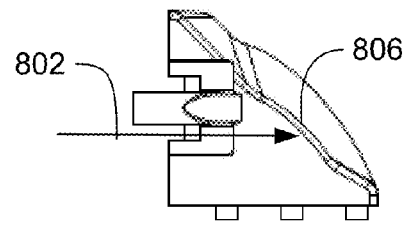
FIG. 10    FIG. 11
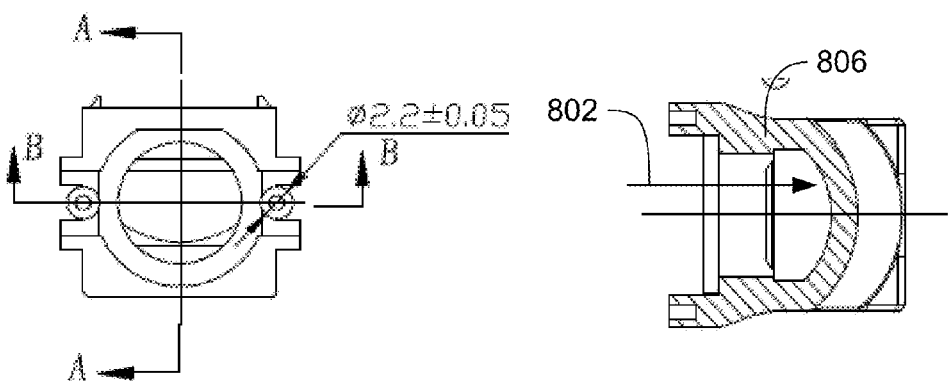
FIG. 12    FIG. 13
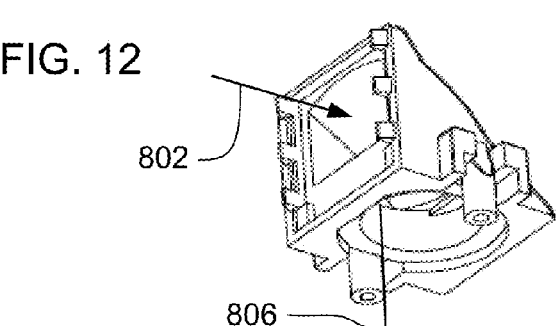
FIG. 14

NON-CONTACT THERMOMETER SENSING A CAROTID ARTERY

RELATED APPLICATION

This application is a continuation of, and claims the benefit under 35 U.S.C. 120 of U.S. Original application Ser. No. 13/624,874 filed 21 Sep. 2012, now U.S. Pat. No. 8,452,382.

FIELD

This disclosure relates generally to digital thermometers, and more particularly to multiple source points in non-contact temperature sensing.

BACKGROUND

Conventional non-contact digital thermometers determine temperature from a source point on a human subject.

BRIEF DESCRIPTION

In one aspect, an apparatus to determine a body temperature from a carotid artery source point includes a housing, a non-contact electromagnetic sensor operably mounted to the housing, the non-contact electromagnetic sensor being operable to receive electromagnetic energy from the carotid artery source point of a subject and operable to generate a numerical representation of the electromagnetic energy of the carotid artery source point, a printed circuit board mounted in the housing, electrically coupled to the non-contact electromagnetic sensor and operable to determine the body temperature of the subject from the numerical representation of the electromagnetic energy of the carotid artery source point, wherein determining the body temperature of the subject further comprises calculating the body temperature from the numerical representation of the electromagnetic energy of the carotid artery source point, a representation of an ambient air temperature reading, a representation of a calibration difference, and a representation of a bias in consideration of the temperature sensing mode and a button operably coupled to the printed circuit board.

In another aspect, an apparatus to measure a body temperature includes a housing, a non-contact sensor operably mounted to the housing, the non-contact sensor having an electromagnetic sensor, the electromagnetic sensor being operable to receive electromagnetic energy from a plurality of body source points of a subject including a carotid source point of the subject and generate a numerical representation of the electromagnetic energy of each of the plurality of body source points, a printed circuit board mounted in the housing and operable to determine the body temperature of the subject from the numerical representation of the electromagnetic energy of each of the plurality of body source points, wherein determining the body temperature of the subject further comprises calculating the body temperature from the numerical representation of the electromagnetic energy of each of the body source points, a representation of an ambient air temperature reading, a representation of a calibration difference, and a representation of a bias in consideration of the temperature sensing mode which yields a calculated body temperature of each of the plurality of source points, and averaging the calculated body temperature of each of the plurality of source points which yields the body temperature and a display device operably coupled to the printed circuit board and operable to display the body temperature.

In yet another aspect, a method to measure body temperature includes sensing electromagnetic energy at a plurality of external source points on a subject which yields a sensed electromagnetic energy of the plurality of external source points, determining the body temperature of the subject from the sensed electromagnetic energy of the plurality of external source points including a carotid source point, the determining being performed by a microprocessor, wherein determining the body temperature of the subject further comprises calculating the body temperature from a numerical representation of the electromagnetic energy of the carotid source point, a representation of an ambient air temperature reading, a representation of a calibration difference, and a representation of a bias in consideration of the temperature sensing mode, and the method further comprising averaging the body temperature of each of the plurality of external source points which yields the body temperature.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 8-14 are block diagrams of a sensor collector to guide electromagnetic energy to measure temperature, according to an implementation;

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, apparatus of implementations are described. In the second section, implementations of methods are described. In the third section, a hardware and the operating environment in conjunction with which implementations may be practiced are described. Finally, in the fourth section, a conclusion of the detailed description is provided.

Apparatus Implementations

In this section, particular apparatus of implementations are described by reference to a series of diagrams.

Figure 1:
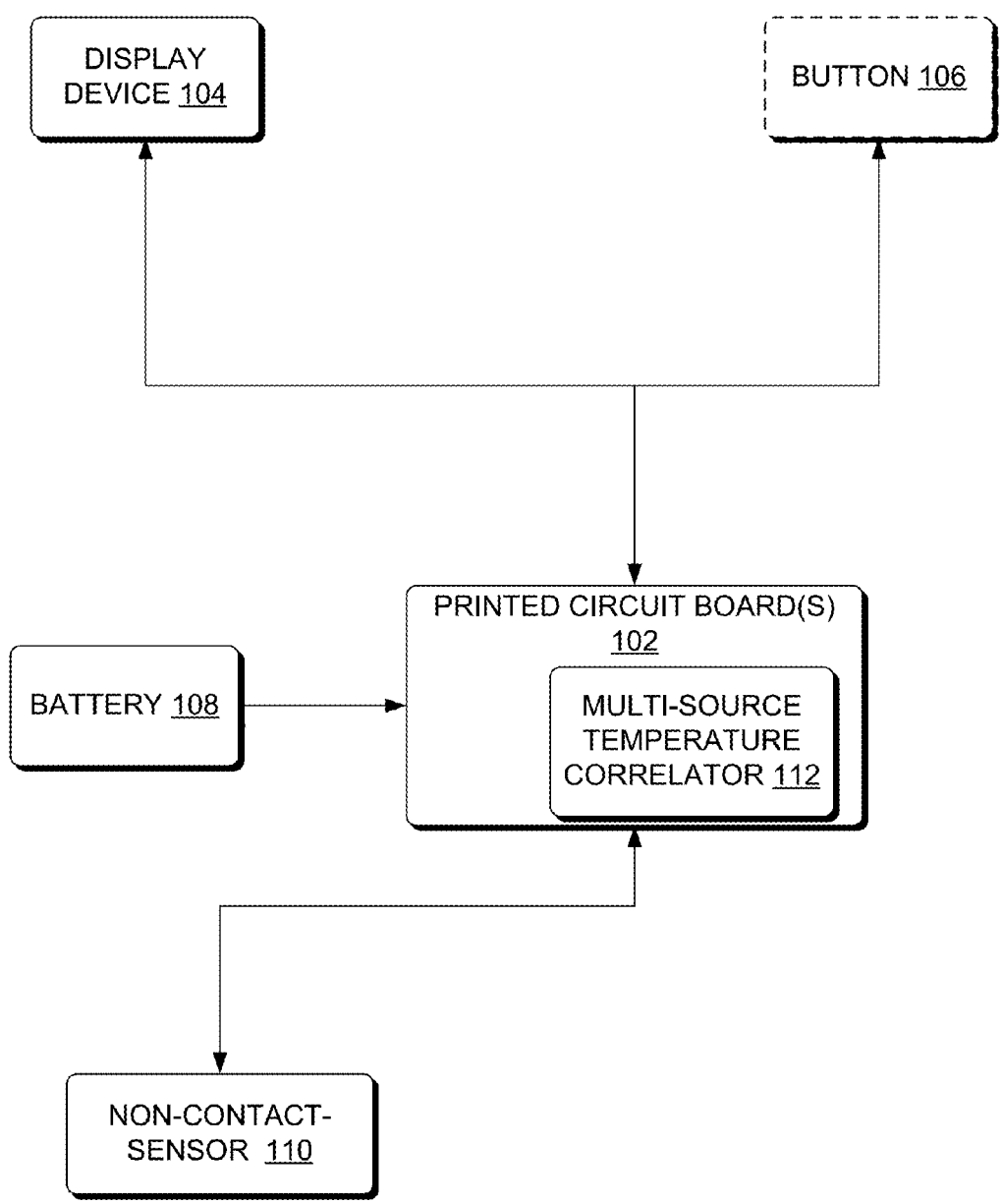
FIG. 1 is a block diagram of apparatus to measure temperature from multiple source points, according to an implementation.

FIG. 1 is a block diagram of apparatus 100 to measure temperature from multiple source points, according to an implementation. A source point is an external point or position. Apparatus 100 is handheld and battery powered for intermittent measurement and monitoring of human or animal body temperature of people of all ages. Apparatus 100 measures electromagnetic energy emitted from multiple source points of the skin surface, such as infrared energy, of the human or animal and direct body temperature. Apparatus 100 is operationally simple enough to be used by consumers in the household environment, yet accurate enough to be used by professional medical facilities.

Apparatus 100 includes one or more printed circuit board(s) 102.

Apparatus 100 also includes a display device 104 that is operably coupled to the one or more printed circuit board(s) 102. Some implementations of apparatus 100 also include a button 106 that is operably coupled to the one or more printed circuit board(s) 102. Apparatus 100 also includes a battery 108, such as a lithium ion battery, that is operably coupled to the one or more printed circuit board(s) 102.

Apparatus 100 also includes a non-contact sensor 110 that is operably coupled to the one or more printed circuit board(s) 102. The non-contact sensor 110 detects temperature in response to remote sensing of a surface a human or animal. In some implementations, the non-contact thermometer is an infrared temperature sensor. All humans or animals radiate infrared energy. The intensity of this infrared energy depends on the temperature of the human or animal, thus the amount of infrared energy emitted by a human or animal can be interpreted as a proxy or indication of the temperature of the human or animal. The non-contact sensor 110 measures the temperature of a human or animal based on the electromagnetic energy radiated by the human or animal. The measurement of electromagnetic energy is taken by the non-contact sensor 110 which constantly analyzes and registers the ambient temperature. When the operator of apparatus 100 holds the non-contact sensor 110 about 5-8 cm (2-3 inches) from the forehead and activates the radiation sensor, the measurement is instantaneously measured. To measure a temperature using the non-contact sensor 110, pushing the button 106 causes a reading of temperature measurement from the non-contact sensor 110 and the measured temperature is thereafter displayed on the display device 104.

Body temperature of a human or animal can be measured in many surface locations of the body. Most commonly, temperature measurements are taken of the forehead, mouth (oral), inner ear (tympanic), armpit (axillary) or rectum. In addition, temperature measurements are taken of a carotid artery (the external carotid artery on the right side of a human neck). An ideal place to measure temperature is the forehead in addition to the carotid artery. When electromagnetic energy is sensed from two or more source points, for example, the forehead and the external carotid artery on the right side of a human neck, a multi-source temperature correlator 112 performs one or more of the correlating actions in the methods as described in FIG. 30-33. The multi-source temperature correlator 112 correlates the temperatures sensed by the non-contact sensor 110 from the multiple source points (e.g. the forehead and the carotid artery) to another temperature, such as a core temperature of the subject, an axillary temperature of the subject, a rectal temperature of the subject and/or an oral temperature of the subject. The multi-source temperature correlator 112 can be implemented as a component on a microprocessor, such as controller chip 3704 in FIG. 37 or read-only memory.

The apparatus 100 also detects the body temperature of a human or animal regardless of the room temperature because the measured temperature of the non-contact sensor 110 is adjusted in reference to the ambient temperature in the air in the vicinity of the apparatus. The human or animal must not have undertaken vigorous physical activity prior to temperature measurement in order to avoid a misleading high temperature. Also, the room temperature should be moderate, 50° F. to 120° F.

The non-contact sensor 110 provides a non-invasive and non-irritating means of measuring human or animal temperature to help ensure good health.

In some implementations, the apparatus 100 includes only one printed circuit board 102, in which case the printed circuit board 102 includes not more than one printed circuit board 102. In some implementations, the apparatus 100 includes two printed circuit boards 102, such as a first printed circuit board and a second printed circuit board. In some implementations, the printed circuit board(s) 102 include a microprocessor. In some implementations, the apparatus 100 includes only one display device 104, in which case the display device 104 includes not more than one display device 104. In some implementations, the display device 104 is a liquid-crystal diode (LCD) display device. In some implementations, the display device 104 is a light-emitting diode (LED) display device. In some implementations, the apparatus 100 includes only one battery 108, which case the battery 108 includes not more than one battery 108.

When evaluating results, the potential for daily variations in temperature can be considered. In children less than 6 months of age daily variation is small. In children 6 months to 2 years old the variation is about 1 degree. By age 6 variations gradually increase to 2 degrees per day. In adults there is less body temperature variation.

While the apparatus 100 is not limited to any particular printed circuit board(s) 102, display device 104, button 106, battery 108, a non-contact sensor 110 and a multi-source temperature correlator 112, for sake of clarity a simplified printed circuit board(s) 102, display device 104, button 106, battery 108, a non-contact sensor 110 and a multi-source temperature correlator 112 are described.

Figure 2:
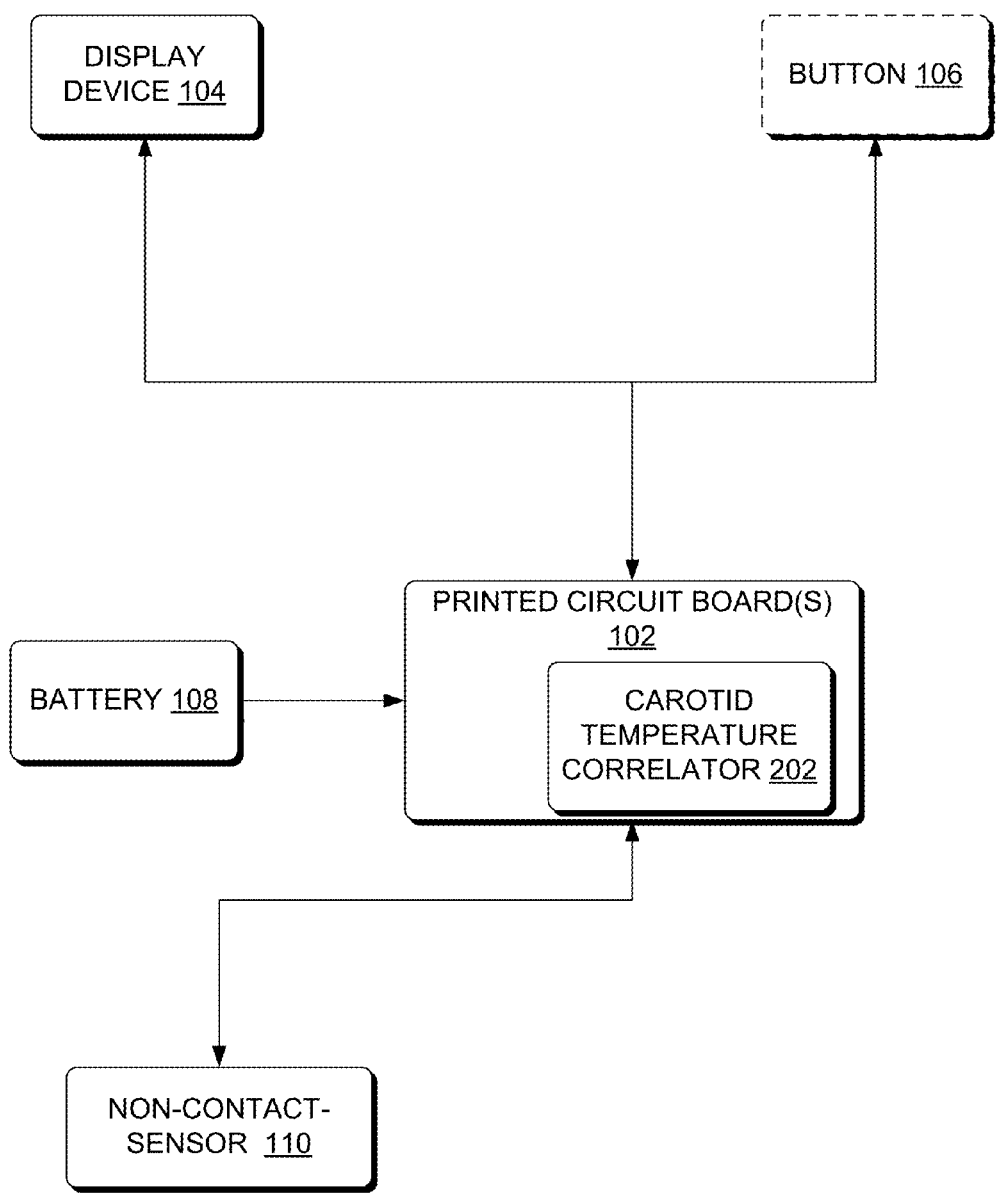
FIG. 2 is a block diagram of apparatus to measure temperature from a carotid source point, according to an implementation.

FIG. 2 is a block diagram of apparatus 200 to measure temperature from a carotid source point, according to an implementation. Apparatus 200 is handheld and battery powered for intermittent measurement and monitoring of human or animal body temperature of people of all ages. Apparatus 200 measures electromagnetic energy, such as infrared energy, emitted from a source point of the skin surface of a carotid artery of the human or animal. Apparatus 200 is operationally simple enough to be used by consumers in the household environment, yet accurate enough to be used by professional medical facilities.

Apparatus 200 includes one or more printed circuit board(s) 102 and a display device 104 that is operably coupled to the one or more printed circuit board(s) 102. Some implementations of apparatus 200 also include a button 106 that is operably coupled to the one or more printed circuit board(s) 102. Apparatus 200 also includes a battery 108, such as a lithium ion battery, that is operably coupled to the one or more printed circuit board(s) 102.

Apparatus 200 also includes a non-contact sensor 110 that is operably coupled to the one or more printed circuit board(s) 102. The non-contact sensor 110 detects temperature in response to remote sensing of a surface a human or animal. When the operator of apparatus 200 holds the non-contact sensor 110 about 5-8 cm (2-3 inches) from the carotid artery and activates the non-contact sensor 110, the measurement is instantaneously measured.

Figure 30:
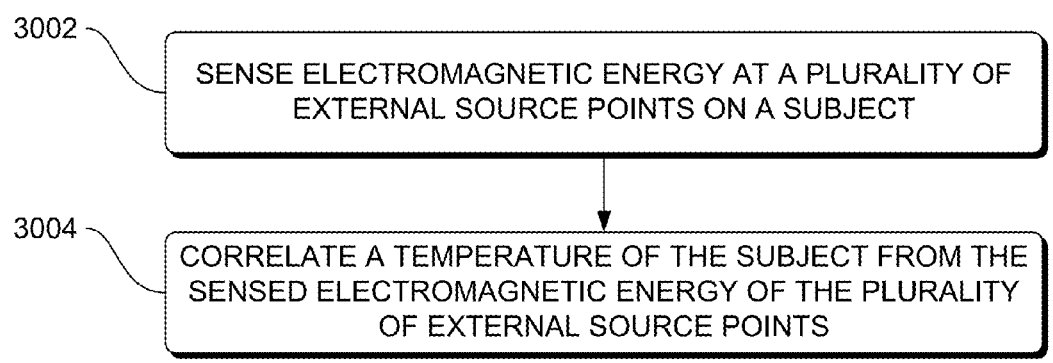
FIG. 30 is a flowchart of a method to measure temperature from multiple source points.
Figure 31:
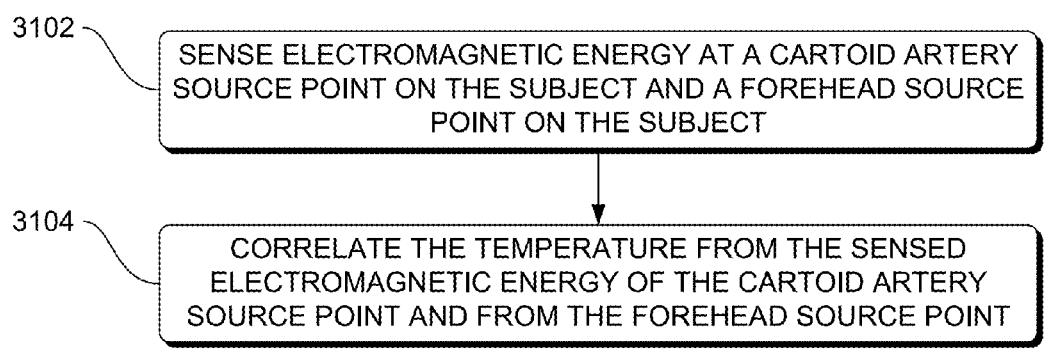
FIG. 31 is a flowchart of a method to measure temperature of a forehead and a carotid artery, according to an implementation.
Figure 32:
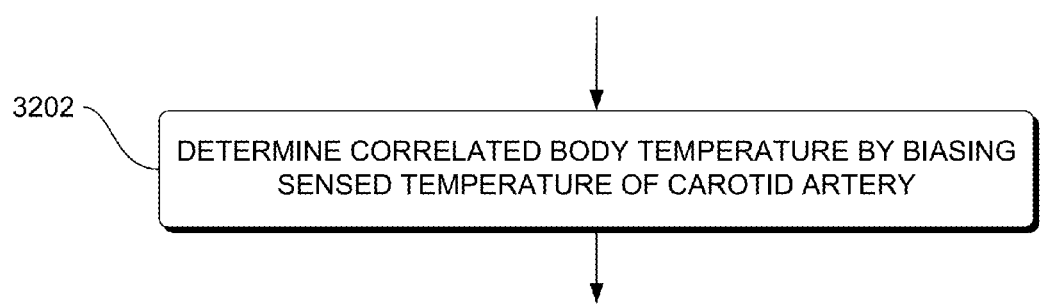
FIG. 32 is a flowchart of a method of determining correlated temperature of a carotid artery, according to an implementation.

When electromagnetic energy is sensed by the non-contact sensor 110 from the carotid artery on the right side of a human neck, a carotid temperature correlator 202 performs one or more of the correlating actions in the methods as described in FIG. 30-32. The carotid temperature correlator 202 correlates the temperatures sensed by the non-contact sensor 110 from the carotid source point to another temperature, such as a core temperature of the subject, an axillary temperature of the subject, a rectal temperature of the subject and/or an oral temperature of the subject. The carotid temperature correlator 202 can be implemented as a component on a microprocessor, such as controller chip 3704 in FIG. 37 or read-only memory.

The apparatus 200 also detects the body temperature of a human or animal regardless of the room temperature because the measured temperature of the non-contact sensor 110 is adjusted in reference to the ambient temperature in the air in the vicinity of the apparatus 200. The human or animal must not have undertaken vigorous physical activity prior to temperature measurement in order to avoid a misleading high temperature. Also, the room temperature should be moderate, 50° F. to 120° F.

In some implementations, the apparatus 200 includes only one printed circuit board 102, in which case the printed circuit board 102 includes not more than one printed circuit board 102. In some implementations, the apparatus 200 includes two printed circuit boards 102, such as a first printed circuit board and a second printed circuit board. In some implementations, the printed circuit board(s) 102 include a microprocessor. In some implementations, the apparatus 200 includes only one display device 104, in which case the display device 104 includes not more than one display device 104. In some implementations, the display device 104 is a liquid-crystal diode (LCD) display device. In some implementations, the display device 104 is a light-emitting diode (LED) display device. In some implementations, the apparatus 200 includes only one battery 108, which case the battery 108 includes not more than one battery 108.

While the apparatus 200 is not limited to any particular printed circuit board(s) 102, display device 104, button 106, battery 108, a non-contact sensor 110 and a carotid temperature correlator 202, for sake of clarity a simplified printed circuit board(s) 102, display device 104, button 106, battery 108, a non-contact sensor 110 and a carotid temperature correlator 202 are described.

Figure 3:
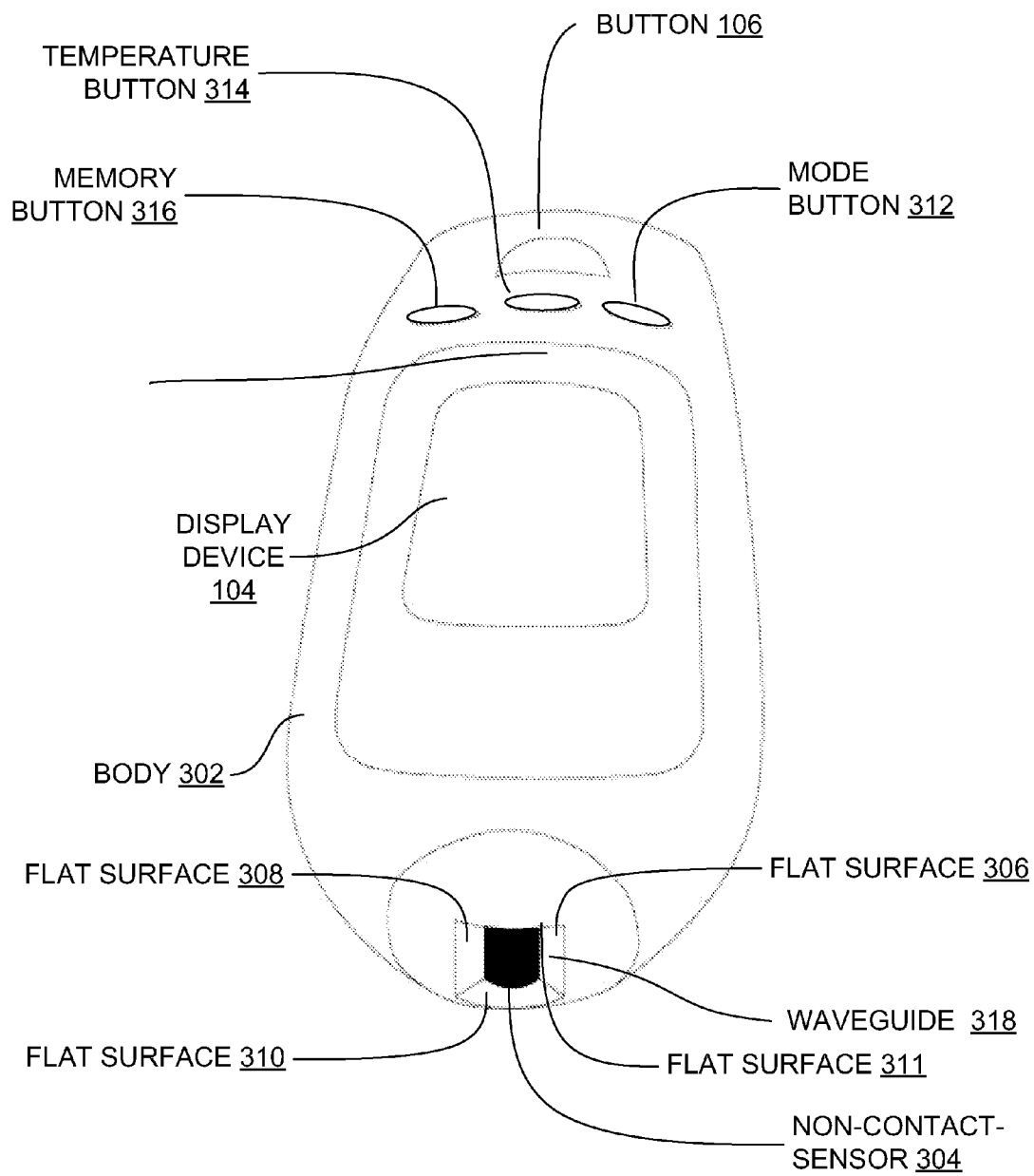
FIG. 3 is an isometric top-view block diagram of an apparatus to measure temperature using both a non-contact thermometer with a right-angled waveguide and not including a contact thermometer, according to an implementation.

FIG. 3 is an isometric top-view block diagram of an apparatus 300 to measure temperature using both a non-contact thermometer with a right-angled waveguide and not including a contact thermometer, according to an implementation. Apparatus 300 is handheld and battery powered for intermittent measurement and monitoring of human or animal body temperature of people of all ages. Apparatus 300 measures non-contact infrared energy emitted from the skin surface of the human or animal. Apparatus 300 can be used by consumers in the household environment.

Apparatus 300 includes the display device 104 that is mounted on the exterior of a body 302 or other housing of the apparatus 300. Apparatus 300 also includes the button 106 that is mounted on the exterior of the body 302 or other housing of the apparatus 300. Apparatus 300 also includes a sensor 303 of the non-contact sensor 110, the sensor 303 being mounted in the interior of the body 302 of the apparatus 300. The non-contact sensor 110 detects temperature in response to remote sensing of a surface a human or animal. The right-angled waveguide 318 is positioned in proximity to the contact sensor 304. The right-angled waveguide 318 includes at least one flat planar surface. The apparatus 300 includes 4 flat planar surfaces 306, 308, 310 and 311.

Apparatus 300 also includes a mode button 312 that when pressed by an operator toggles or switches between three different detection modes, a first detection mode being detection and display of surface temperature, a second detection mode being detection and display of body temperature and a third detection mode being detection and display of room temperature.

Apparatus 300 also includes a temperature button 314 that when pressed by an operator toggles or switches between two different temperature modes, a first temperature mode being display of temperature in Celsius and a second temperature mode being display of temperature in Fahrenheit.

Apparatus 300 also includes a memory button 316 that when pressed by an operator toggles or switches between a plurality of past temperature readings. In one implementation, the plurality of past temperature readings is 32.

Figure 4:
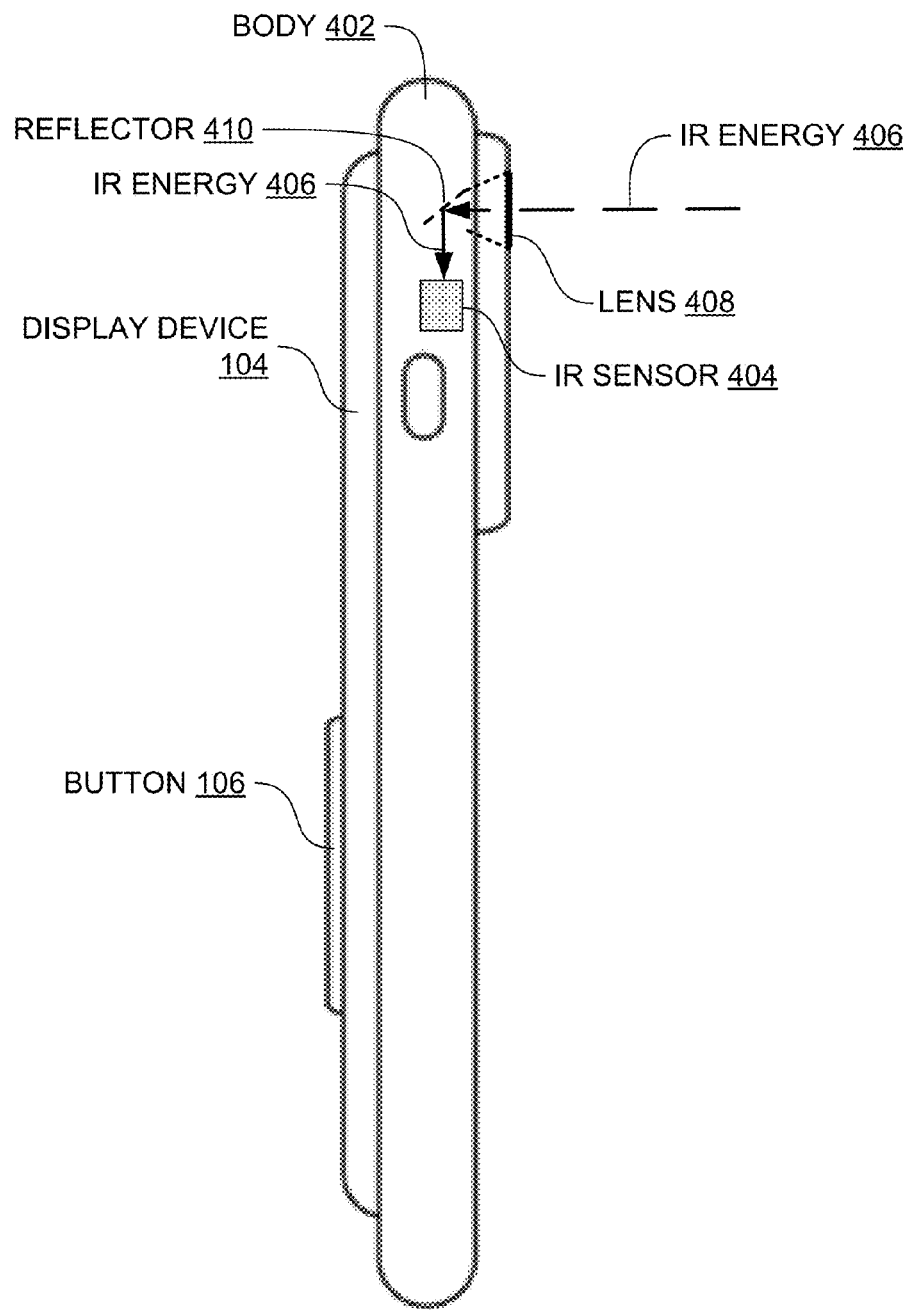
FIG. 4 is a side-view block diagram of an apparatus to measure temperature using a non-contact thermometer with a right-angled waveguide, according to an implementation.

FIG. 4 is a side-view block diagram of an apparatus 400 to measure temperature using a non-contact thermometer with a right-angled waveguide, according to an implementation. Apparatus 400 is handheld and battery powered for intermittent measurement and monitoring of human or animal body temperature of people of all ages. Apparatus 400 measures non-contact infrared energy emitted from the skin surface of the human or animal. Apparatus 400 can be used by consumers in the household environment.

Apparatus 400 includes the display device 104 that is mounted on the exterior of a body 402 or other housing of the apparatus 400. Apparatus 400 also includes the button 106 that is mounted on the exterior of the body 402 or other housing of the apparatus 400.

Apparatus 400 includes the non-contact sensor having an infrared sensor 404. The infrared sensor 404 is operable to receive infrared energy 406 via a pathway to the infrared sensor 404. Apparatus 400 includes a lens 408 that is positioned over the pathway. In some implementations, the lens 408 has only right-angled edges, the lens 408 being square in geometry, that is transverse to the pathway to the infrared sensor 404. The pathway intersects the lens 408. A reflector 410 that is positioned at a 45 degree angle to the infrared sensor 404. The lens 408 has a longitudinal axis that is perpendicular to a longitudinal axis of the infrared sensor. The reflector 410 is positioned at a 45 degree angle to the lens 408. The pathway is coincident to the IR energy 406 that passes through the lens 408, reflects off of the reflector 410 and to the IR sensor 404.

Apparatus 400 also includes the sensor 303 of the non-contact sensor 110, the sensor 303 being mounted in the interior of the body 302 of the apparatus 400. The non-contact sensor 110 detects temperature in response to remote sensing of a surface of a human or animal. The contact sensor 412 detects temperature in response to direct contact with the human or animal. The dual sensors 110 and 412 provide improved convenience and heightened accuracy in detecting temperatures in humans or animals. In some situations, the non-contact sensor 110 is used as initial instrument of temperature detection of a human or animal and the contact sensor 412 is used as a second instrument of temperature detection of the human or animal.

Figure 5:
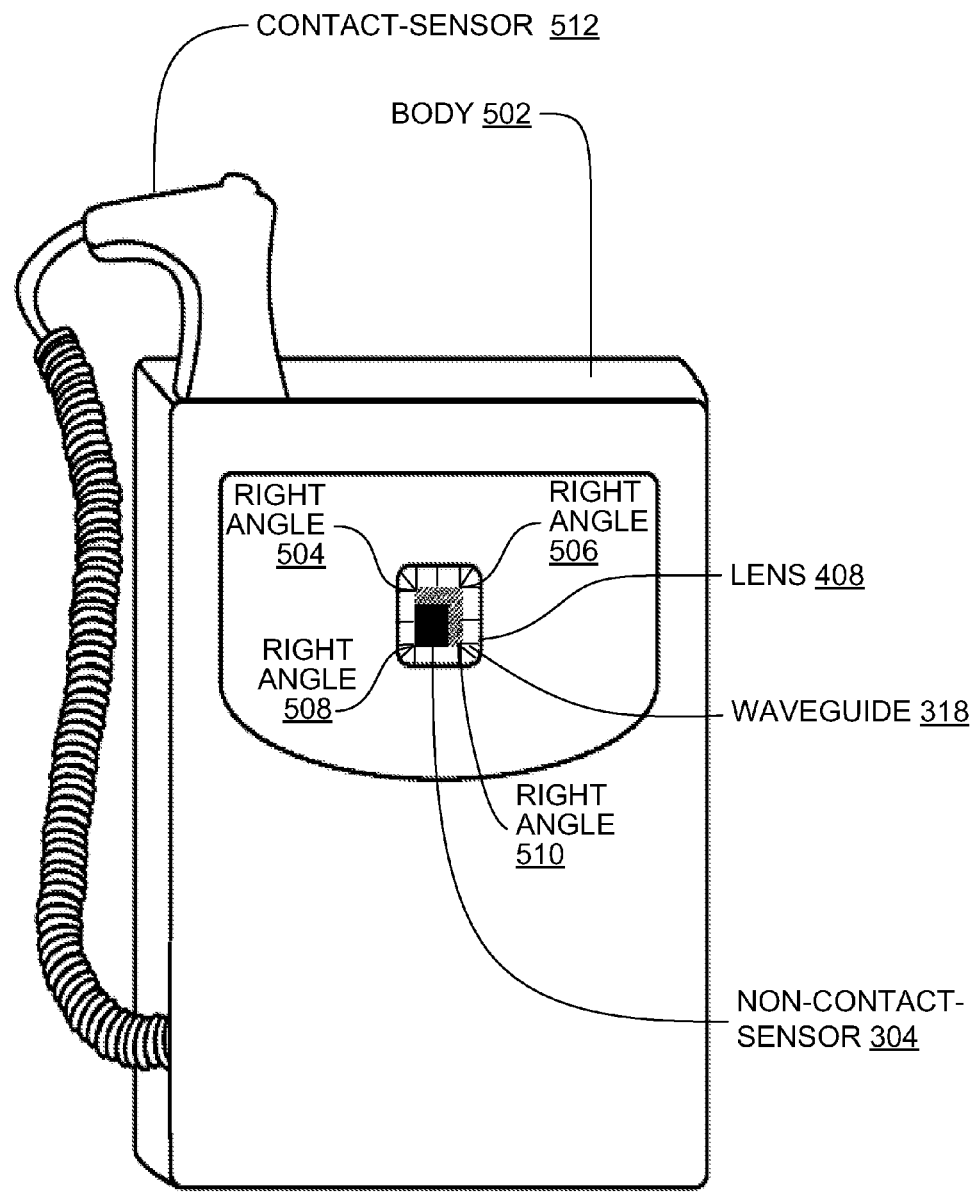
FIG. 5 is an isometric block diagram of an apparatus to measure temperature using both non-contact thermometer with a right-angled waveguide and contact thermometer, according to an implementation.

FIG. 5 is an isometric block diagram of an apparatus 500 to measure temperature using both non-contact thermometer with a right-angled waveguide and a contact thermometer, according to an implementation. Apparatus 500 is handheld and battery powered for intermittent measurement and monitoring of human or animal body temperature of people of all ages. Apparatus 500 measures both infrared energy emitted from the skin surface of the human or animal and direct body temperature. Apparatus 500 can be used by consumers in the household environment.

Apparatus 500 includes the display device 104 that is mounted on the exterior of a body 502 of the apparatus 500. Apparatus 500 also includes the button 106 that is mounted on the exterior of the body 502 of the apparatus 500. Apparatus 500 also includes a lens 408 of the non-contact sensor 110, the lens 408 being mounted on the exterior of the body 502 of the apparatus 500. The non-contact sensor 110 behind the non-contact sensor 404 detects temperature in response to remote sensing of a surface a human or animal. A right-angled waveguide 318 is positioned in proximity to the non-contact sensor 110. The right-angled waveguide 318 includes at least one flat planar surface and right angles 504, 506, 508 and 510. Apparatus 500 also includes the contact sensor 412 that is mounted on the exterior of the body 502 of the apparatus 500. The contact sensor 412 detects temperature in response to direct contact with the human or animal. The dual sensors 110 and 412 provide both convenience and heightened accuracy in detecting temperatures in humans or animals. In some situations, the non-contact sensor 110 is used as an initial instrument of temperature detection of a human or animal and the contact sensor 412 is used as a second instrument of temperature detection of the human or animal.

Figure 6:
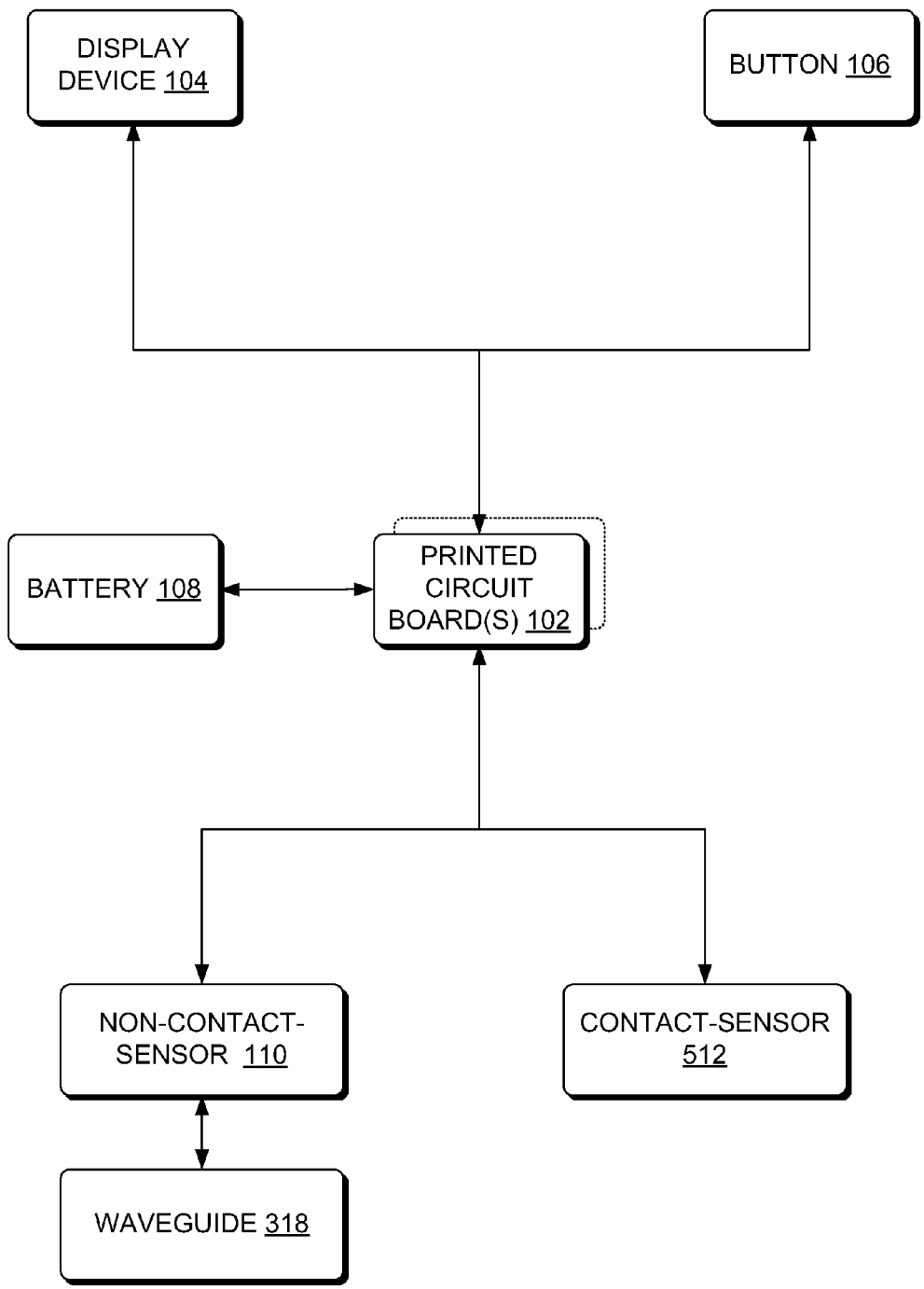
FIG. 6 is a block diagram of apparatus to measure temperature, according to an implementation having a right-angled waveguide.

FIG. 6 is a block diagram of apparatus 600 to measure temperature, according to an implementation. Apparatus 600 is handheld and battery powered for intermittent measurement and monitoring of human or animal body temperature of people of all ages. Apparatus 600 measures both electromagnetic energy emitted from the skin surface, such as infrared energy, of the human or animal and direct body temperature. Apparatus 600 is operationally simple enough to be used by consumers in the household environment, yet accurate enough to be used by professional medical facilities.

Apparatus 600 includes one or more printed circuit board(s) 102.

Apparatus 600 also includes a display device 104 that is operably coupled to the one or more printed circuit board(s) 102. Some implementations of apparatus 600 also include a button 106 that is operably coupled to the one or more printed circuit board(s) 102. Apparatus 600 also includes a battery 108, such as a lithium ion battery, that is operably coupled to the one or more printed circuit board(s) 102.

Apparatus 600 also includes a non-contact sensor 110 that is operably coupled to the one or more printed circuit board(s) 102. The non-contact sensor 110 detects temperature in response to remote sensing of a surface a human or animal. In some implementations the non-contact thermometer is an infrared temperature sensor.

Some implementations of apparatus 600 also include a contact sensor 512 that is operably coupled to the one or more printed circuit board(s) 102. The contact sensor 512 detects temperature in response to direct contact with a human or animal.

A right-angled waveguide 318 is positioned in proximity to the non-contact sensor 110. The geometry of the right-angled waveguide 318 has at least one right-angle and at least flat planar surface. In some implementations, the geometry of the right-angled waveguide 318 has only right-angled edges. In general, a waveguide is a structure of a passageway or pathway which guides waves, such as electromagnetic waves. Waves in open space propagate in all directions, as spherical waves. In this way the wave lose power proportionally to the square of the distance; that is, at a distance R from the source, the power is the source power divided by R2. The waveguide confines the wave to propagation in one dimension, so that (under ideal conditions) the wave loses no power while propagating. Waves are confined inside the waveguide due to total reflection from the waveguide wall, so that the propagation inside the waveguide can be described approximately as a "zigzag" between the walls. There are different types of waveguides for each type of wave. The original and most common implementation of a waveguide is a hollow conductive metal pipe used to carry high frequency radio waves, particularly microwaves. Waveguides differ in their geometry which can confine energy in one dimension such as in slab waveguides or a waveguide can confine energy in two dimensions as in fiber or channel waveguides. As a rule of thumb, the width of a waveguide needs to be of the same order of magnitude as the wavelength of the guided wave.

A conventional geometry of a waveguide has a circular cross-section, which is most useful for gathering electromagnetic waves that have a rotating, circular polarization in which the electrical field traces out a helical pattern as a function of time. However, infrared energy emitted from a surface of a human does not have a rotating, circular polarization in which the electrical field traces out a helical pattern as a function of time. Therefore, in apparatus that measures infrared energy of a human as a proxy of temperature of the human, circular and rounded waveguides should not be used. The waveguide 318 is not conical in geometry because a conical waveguide reflects the electromagnetic waves in a somewhat incoherent manner in which the electromagnetic waves are received at the sensor with a decreased degree of coherency, thus decreasing the signal strength; and the conical waveguide reflects a significant portion of electromagnetic waves out of the waveguide and away from the sensor, thus further reducing the signal strength of the electromagnetic waves received by the sensor and therefore further reducing the accuracy and speed of the non-contact temperature sensing. More specifically, waveguide 318 is not a conical funnel in which the conical funnel has an opening at one end of a longitudinal axis that has a larger diameter than an opening at the other end of the longitudinal axis.

The dual sensors 110 and 412 provide improved convenience and heightened accuracy in detecting temperatures in humans or animals. In some situations, the non-contact sensor 110 is used as an initial instrument of temperature detection of a human or animal and the contact sensor 412 is used as a second instrument of temperature detection of the human or animal. The non-contact sensor 110 eliminates need for contact with the skin, yet the contact sensor 412 provides a more accurate detection of human or animal body temperature to supplement or verify the temperature detected by the non-contact sensor 110.

In some implementations, the apparatus 600 includes only one printed circuit board 102, in which case the printed circuit board 102 includes not more than one printed circuit board 102. In some implementations, the apparatus 600 includes two printed circuit boards 102, such as a first printed circuit board and a second printed circuit board. In some implementations, the printed circuit board(s) 102 include a microprocessor. In some implementations, the apparatus 600 includes only one display device 104, in which case the display device 104 includes not more than one display device 104. In some implementations, the display device 104 is a liquid-crystal diode (LCD) display device. In some implementations, the display device 104 is a light-emitting diode (LED) display device. In some implementations, the apparatus 600 includes only one battery 108, which case the battery 108 includes not more than one battery 108.

While the apparatus 600 is not limited to any particular printed circuit board(s) 102, display device 104, button 106, battery 108, non-contact sensor 110 and a contact sensor 412, for sake of clarity a simplified printed circuit board(s) 102, display device 104, button 106, battery 108, non-contact sensor 110 and a contact sensor 412 are described.

Figure 7:
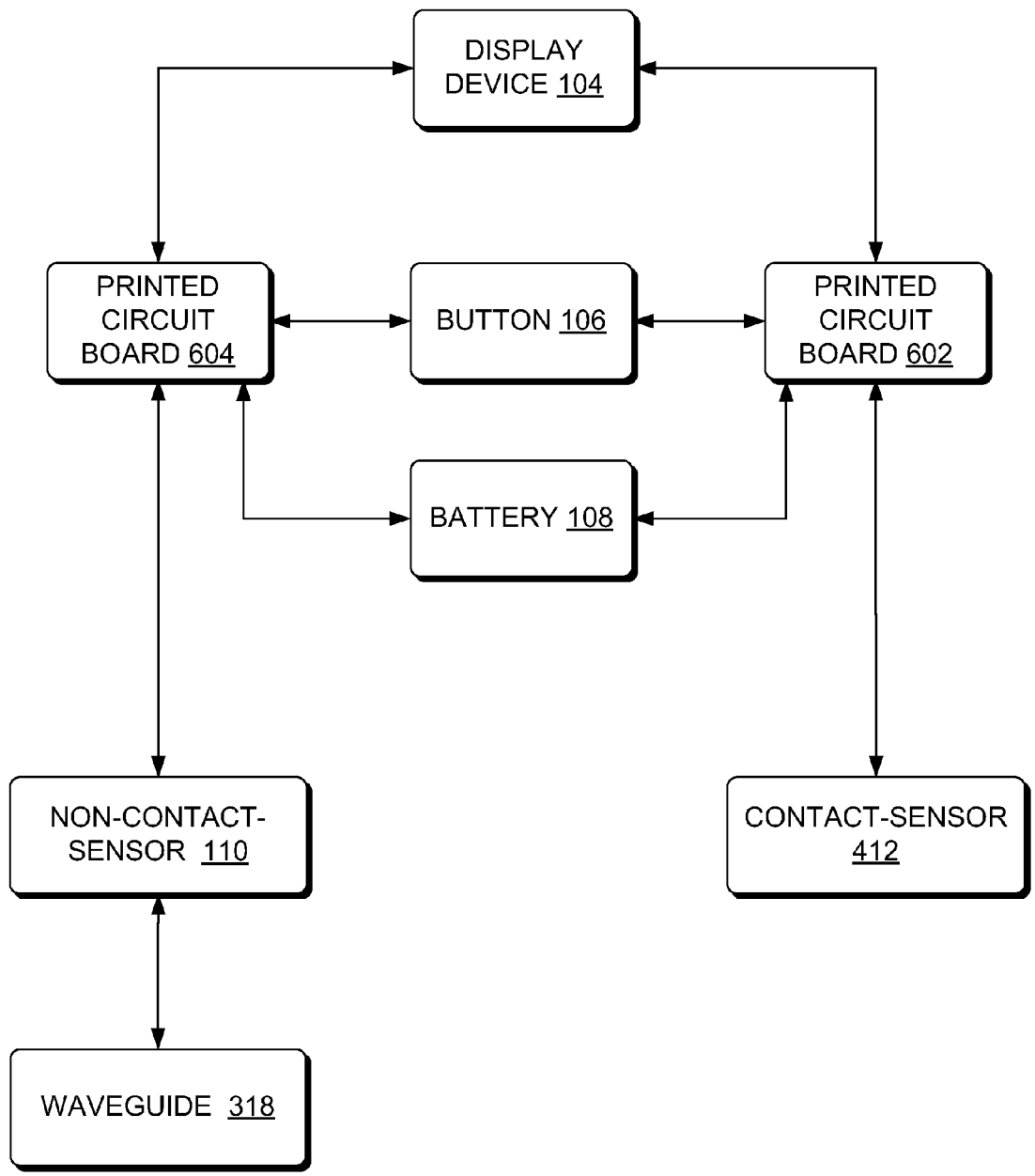
FIG. 7 is a block diagram of apparatus to measure temperature, according to an implementation in which each of a non-contact thermometer and a contact thermometer are controlled by a separate printed circuit board and the non-contact thermometer has a right-angled waveguide, according to an implementation.

FIG. 7 is a block diagram of apparatus 700 to measure temperature, according to an implementation in which each of a non-contact thermometer and a contact thermometer are controlled by a separate printed circuit board and the non-contact thermometer has a right-angled waveguide, according to an implementation.

Apparatus 700 includes the contact sensor 412 that is operably coupled to a first printed circuit board 702, a non-contact sensor 110 that is operably coupled to a second printed circuit board 704, the display device 104 that is operably coupled to the first printed circuit board 702 and the second printed circuit board 704, the button 106 that is operably coupled to the first printed circuit board 702 and the second printed circuit board 704 and the battery 108 that is operably coupled to the first printed circuit board 702 and the second printed circuit board 704. In apparatus 700, the display device 104, the button 106 and the battery 108 are shared, but each thermometer has a dedicated printed circuit board.

A right-angled waveguide 318 is positioned in proximity to the non-contact sensor 110. The geometry of the right-angled waveguide 318 has at least one right-angle. In some implementations, the geometry of the right-angled waveguide 318 has only right-angled edges.

Some implementations of apparatus in FIG. 1-6 include an ambient air temperature sensor that is operably coupled to, or a part of, the printed circuit board(s) 102, 702 or 704.

FIG. 8-14 are block diagrams of a sensor collector to guide electromagnetic energy to measure temperature, according to an implementation. FIG. 8 is a side cut-away view of the sensor collector to guide electromagnetic energy. The electromagnetic energy 802 enters the cavity 804 of the sensor collector and reflects off of the shroud 806 and through the bottom opening. The shroud 806 has in an inside surface that is concave. The shroud 806 is one example of the reflector 410 in FIG. 4. FIG. 9 is a top view of the sensor collector to guide electromagnetic energy. FIG. 10 is a front view of the sensor collector to guide electromagnetic energy. FIG. 11 is a side view of the sensor collector to guide electromagnetic energy. FIG. 12 is a bottom view of the sensor collector to guide electromagnetic energy. FIG. 13 is a top cut-away view of the sensor collector to guide electromagnetic energy. FIG. 14 is a bottom isometric view of the sensor collector to guide electromagnetic energy.

Figure 15:
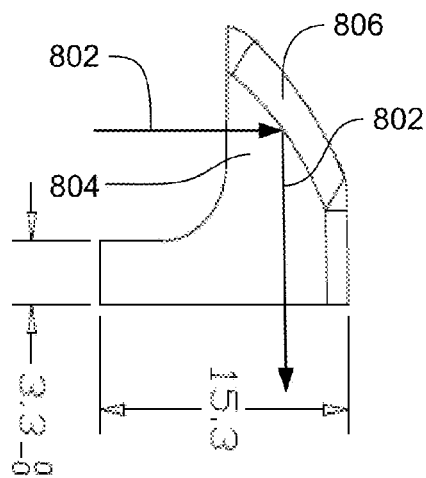
FIG. 15-20 are block diagrams of a shroud of a sensor collector to guide electromagnetic energy to measure temperature, according to an implementation.
Figure 16:
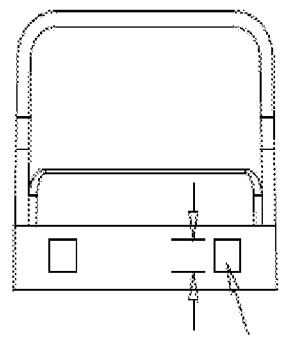
Figure 17:
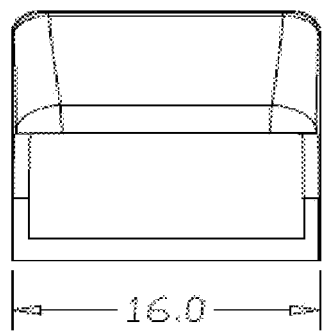
Figure 18:
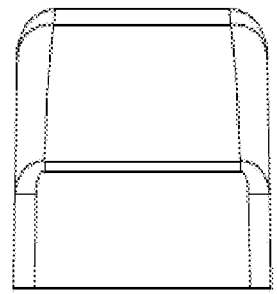
Figure 19:
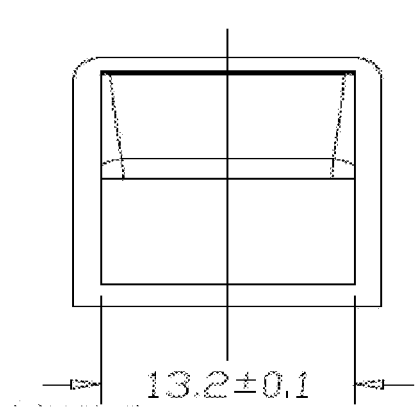
Figure 20:
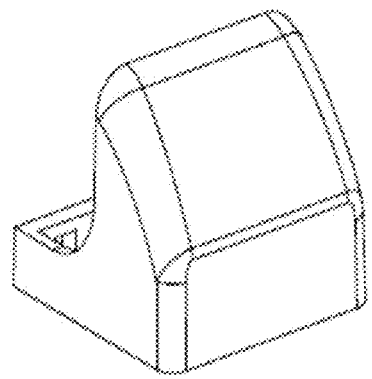

FIG. 15-20 are block diagrams of a shroud of a sensor collector to guide electromagnetic energy to measure temperature, according to an implementation. FIG. 15 is a side view of a shroud of a sensor collector to guide electromagnetic energy. The electromagnetic energy 802 enters the cavity 804 of the sensor collector and reflects off of the shroud 806 and through the bottom opening. FIG. 16 is a bottom view of a shroud of a sensor collector to guide electromagnetic energy. FIG. 17 is a front cut-away view of a shroud of a sensor collector to guide electromagnetic energy. FIG. 18 is a front view of a shroud of a sensor collector to guide electromagnetic energy. FIG. 19 is a front cut-away view of a shroud of a sensor collector to guide electromagnetic energy. FIG. 20 is a back top isometric view of a shroud of a sensor collector to guide electromagnetic energy.

Figure 21:
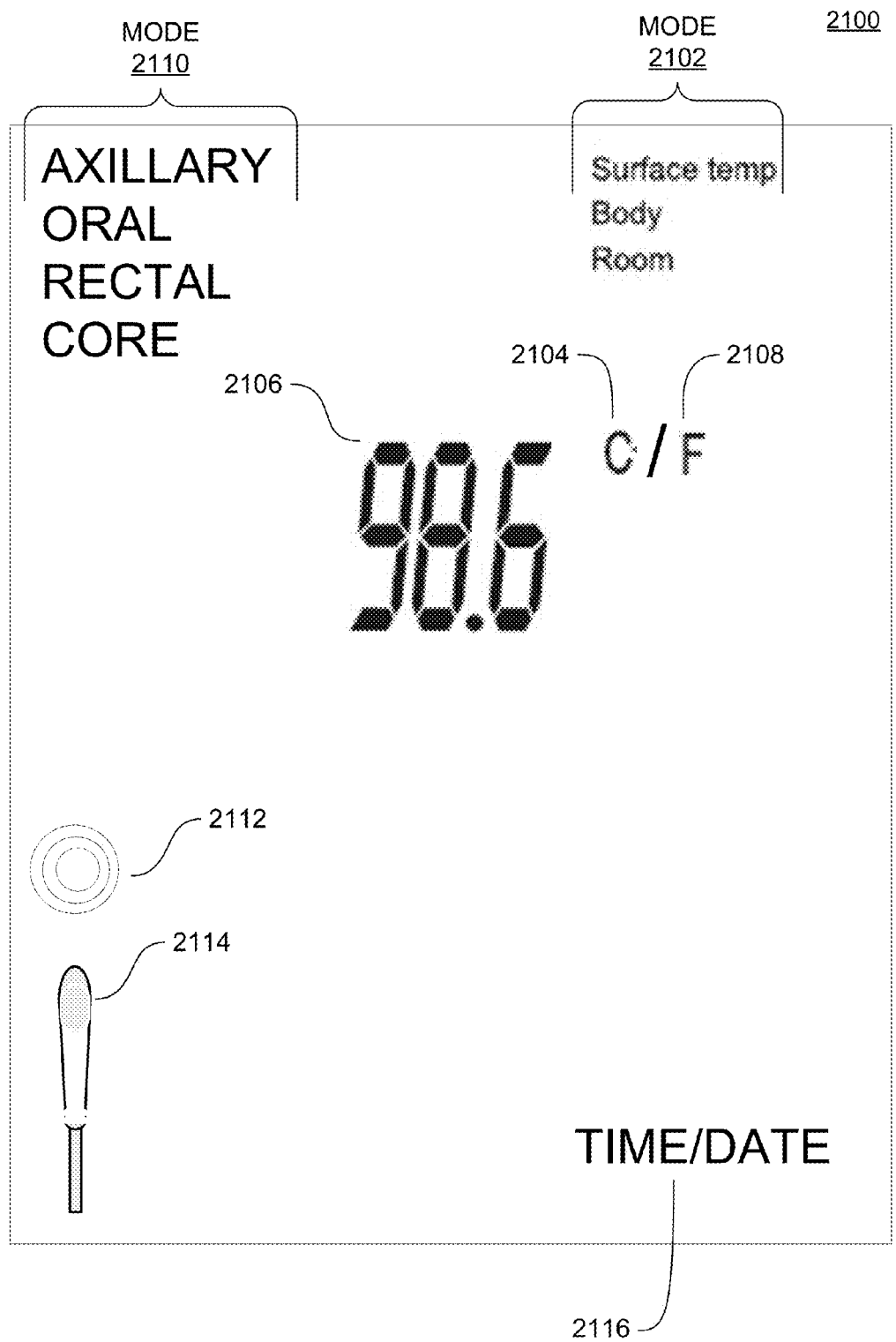
FIG. 21 is a representation of display that is presented on the display device of apparatus in FIG. 1-6, according to an implementation that manages both a non-contact sensor and a contact sensor.

FIG. 21 is a representation of display that is presented on the display device of apparatus in FIG. 1-6, according to an implementation that manages both a non-contact sensor and a contact sensor.

Some implementations of display 2100 include a representation of three detection modes 2102, a first detection mode being detection and display of surface temperature, a second detection mode being detection and display of body temperature and a third detection mode being detection and display of room temperature.

Some implementations of display 2100 include a representation of Celsius 2104 that is activated when the apparatus is in Celsius mode.

Some implementations of display 2100 include a representation of a sensed temperature 2106.

Some implementations of display 2100 include a representation of Fahrenheit 2108 that is activated when the apparatus is in Fahrenheit mode.

Some implementations of display 2100 include a representation of a mode 2110 of site temperature sensing, a first site mode being detection of an axillary surface temperature, a second site mode being detection of an oral temperature, a third site mode being detection of a rectal temperature and a fourth site mode being detection of a core temperature.

Some implementations of display 2100 include a representation of a scanner mode 2112 that is activated when the sensed temperature 2106 is from a non-contact sensor 110.

Some implementations of display 2100 include a representation of a probe mode 2114 that is activated when the sensed temperature 2106 is from a contact sensor 412.

Some implementations of display 2100 include a representation of the current time/date 2116 of the apparatus.

Figure 22:
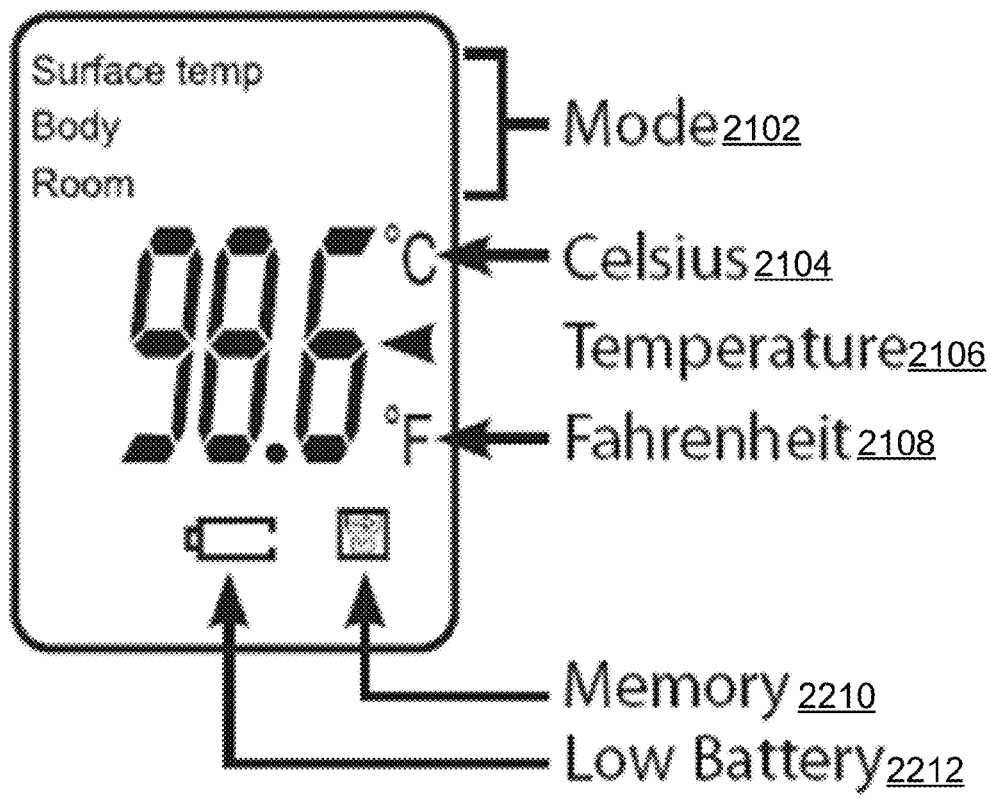
FIG. 22 is a representation of display that is presented on the display device of apparatus in FIG. 1-6, according to an implementation.

FIG. 22 is a representation of display 2200 that is presented on the display device of apparatus in FIG. 1-6, according to an implementation.

Some implementations of display 2200 include a representation of three detection modes 2102, a first detection mode being detection and display of surface temperature, a second detection mode being detection and display of body temperature and a third detection mode being detection and display of room temperature.

Some implementations of display 2200 include a representation of Celsius 2104 that is activated when the apparatus is in Celsius mode.

Some implementations of display 2200 include a representation of a temperature 2106.

Some implementations of display 2200 include a representation of Fahrenheit 2108 that is activated when the apparatus is in Fahrenheit mode.

Some implementations of display 2200 include a representation of memory 2210.

Some implementations of display 2200 include a representation of battery charge level 2212.

Figure 23:
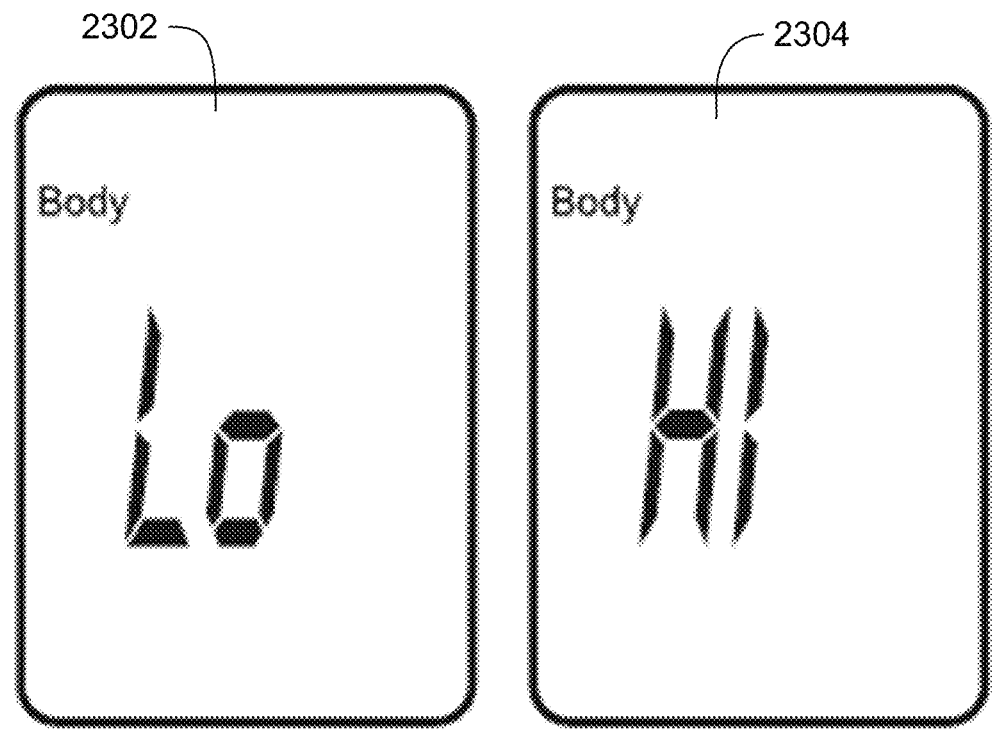
FIG. 23 is a representation of text displays that are presented on the display device of apparatus in FIG. 1-6, according to an implementation.

FIG. 23 is a representation of text displays 2300 that are presented on the display device of apparatus in FIG. 1-6, according to an implementation. Some implementations of display 2300 include a text representation that a sensed body temperature 2302 is "Lo" as in "low". Some implementations of display 2300 include a text representation that a sensed body temperature 2304 is "Hi" as in "high".

FIG. 24-29 are representations of graphical displays that are presented on the display device of apparatus in FIG. 1-6, according to implementations. The double-arrow bracket 2402 in FIG. 24-29 represents a general range of normal temperatures.

Figures 24, 25, 26:
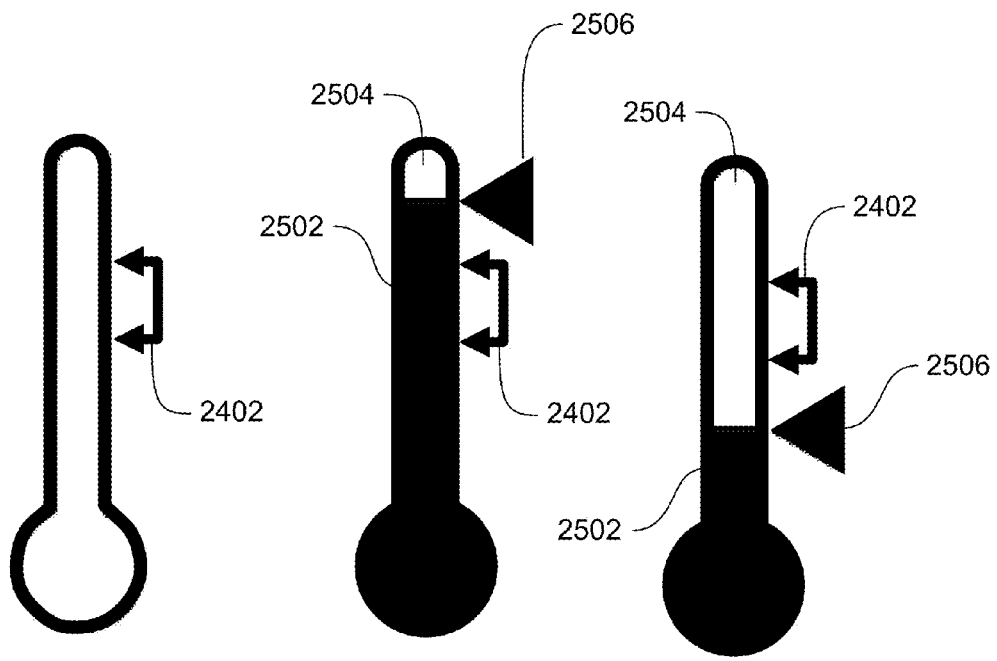
FIG. 24-29 are representations of graphical displays that are presented on the display device of apparatus in FIG. 1-6, according to implementations.

FIG. 24 is a graphical display that represents a state of having no sensed temperature. The empty thermometer in FIG. 24 indicates that no temperature sensing activity has completed.

FIG. 25 is a graphical display that represents a state of having sensed a high temperature. The thermometer in FIG. 25 having a contrasting color 2502 that is located above the general ranges of normal temperature indicates a higher than normal temperature. In FIG. 25-29, the contrasting color 2502 contrasts to the remainder 2504 of the interior of the thermometer image. In the example shown in FIG. 25-29, the contrasting color 2502 is black which contrasts with the white of the remainder 2504 of the interior of the thermometer image. FIG. 25 includes a pointer 2506 indicating the sensed temperature.

FIG. 26 is a graphical display that represents a state of having sensed a low temperature. The thermometer in FIG. 26 having only a contrasting color that is located below the general ranges of normal temperature indicates a lower than normal temperature. FIG. 26 includes a pointer 2506 indicating the sensed temperature.

Figures 27, 28, 29:
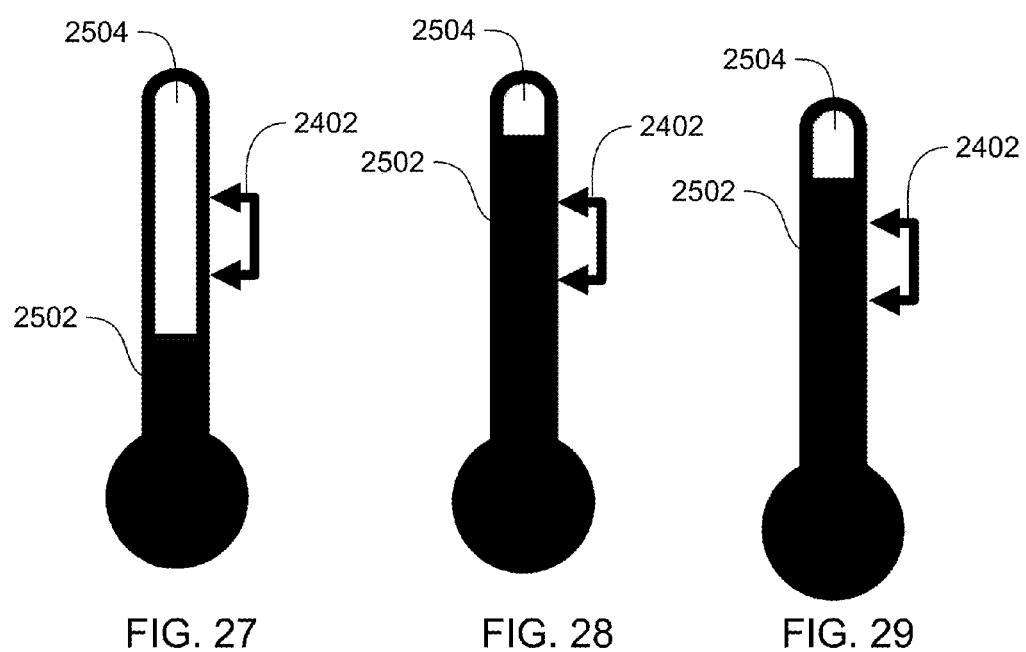

FIG. 27 is a graphical display that represents a state of having sensed a low temperature. The thermometer in FIG. 27 having contrasting color located only below the general ranges of normal temperature indicates a lower than normal temperature.

FIG. 28 is a graphical display that represents a state of having sensed a high temperature. The thermometer in FIG. 28 having contrasting color that is located above the general ranges of normal temperature indicates a higher than normal temperature.

FIG. 29 is a graphical display that represents a state of having sensed a high temperature. The thermometer in FIG. 29 having contrasting color that is located above the general ranges of normal temperature indicates a higher than normal temperature.

Use Cases of Apparatus

In one example of use of the apparatus shown in FIG. 1-6, an operator performs a scan with the non-contact sensor 110, the operator determines that a contact temperature is helpful or necessary and the operator performs a reading with a contact sensor 412. In another example of use of the apparatus shown in FIG. 1-6, the operator performs a reading with the contact sensor 412, the operator determines that a non-contact temperature is helpful or necessary and the operator performs a scan with the non-contact sensor 110.

To perform a scan with the non-contact sensor 110, the operator uses a button to select one three modes of the apparatus, 1) oral 2) rectal or 4) axillary. The operator pushes the scan button 106 to initiate a non-contact temperature scan. The apparatus displays the detected temperature that is calculated in reference to the selected mode.

To determine that a contact temperature is helpful or necessary, the operator reviews the temperature displayed by the apparatus and determines that a temperature reading using a different technique, such as either contact or non-contact) would be informative.

To perform a reading with the contact sensor 412, the operator removes a contact sensor 412 probe from a receiver and places a disposable probe cover over the contact sensor 412, and the operator inserts the probe of the contact sensor 412 into the mouth of a human or animal. The apparatus senses in increase in temperature through the contact sensor 412 and in response the apparatus starts a timer. After expiration of the timer, the apparatus displays on the display device 104 the sensed temperature at the time of the timer expiration and generates an audio alert and in response the operator removes the probe of the contact sensor 412 from the mouth of the human or animal, places the probe of the contact sensor 412 into the receiver and reads the displayed temperature on the display device 104.

Method Implementations

In the previous section, apparatus of the operation of an implementation was described. In this section, the particular methods performed by apparatus 100, 200, 400, 500 and 700 of such an implementation are described by reference to a series of flowcharts.

FIG. 30 is a flowchart of a method 3000 to measure temperature from multiple source points. Method 3000 includes sensing electromagnetic energy at a plurality of external source points on a subject, at block 3002. The sensing at block 3000 yields a sensed electromagnetic energy of the plurality of external source points. In one implementation, block 3002 includes sensing the electromagnetic energy from only at the carotid artery source point on the subject and sensing the electromagnetic energy at no other point on the subject.

Method 3000 also includes correlating a temperature of the subject from the sensed electromagnetic energy of the plurality of external source points, at block 3004. The correlating at block 3004 yields a correlated temperature. In some implementations, the correlating at block 3004 is performed by the multi-source temperature correlator 112 in FIG. 1. In some implementations, block 3004 includes correlating only the temperature of the subject from the sensed electromagnetic energy of the carotid artery source point on the subject. In one implementation, block 3004 includes correlating the electromagnetic energy from only the carotid artery source point on the subject and correlating the electromagnetic energy at no other point on the subject.

FIG. 31 is a flowchart of a method 3100 to measure temperature of a forehead and a carotid artery, according to an implementation. Method 3100 includes sensing the electromagnetic energy at the carotid artery source point on the subject and/or the forehead source point on the subject, at block 3102. In one implementation, block 3102 includes sensing the electromagnetic energy from only at the carotid artery source point on the subject and sensing the electromagnetic energy at no other point on the subject. The sensing at block 3102 yields the sensed electromagnetic energy of the external source point(s).

Method 3100 also includes correlating the temperature of the subject from the sensed electromagnetic energy of the carotid artery source point on the subject and/or from the forehead source point on the subject, at block 3104. The correlating at block 3104 yields a correlated temperature. In some implementations, block 3104 includes correlating only the temperature of the subject from the sensed electromagnetic energy of the carotid artery source point on the subject. In some implementations, the correlating at block 3104 is performed by the multi-source temperature correlator 112 in FIG. 1. In one implementation, block 3104 includes correlating the electromagnetic energy from only the carotid artery source point on the subject and correlating the electromagnetic energy at no other point on the subject.

In some implementations of method 3000 and 3100, the correlated temperature of the subject includes only a core temperature of the subject, an axillary temperature of the subject, a rectal temperature of the subject and an oral temperature of the subject. Methods 3000 and 3100 permit an operator to take the temperature of a subject at multiple locations on a patient and from the temperatures at multiple locations to determine the temperature at a number of other locations of the subject. The multiple source points of which the electromagnetic energy is sensed are mutually exclusive to the location of the correlated temperature. In one example, the carotid artery source point on the subject and a forehead source point are mutually exclusive to the core temperature of the subject, an axillary temperature of the subject, a rectal temperature of the subject and an oral temperature of the subject.

The correlation of action 3004 in FIG. 30 and action 3104 can include a calculation based on Formula 1:

$$T_{body} = |f_{stb}(T_{surface\ temp} + f_{ntc}(T_{ntc})) + F4_{body}| \quad \text{Formula 1}$$

where $T_{body}$ is the temperature of a body or subject where $f_{stb}$ is a mathematical formula of a surface of a body where $f_{ntc}$ is mathematical formula for ambient temperature reading where $T_{surface\ temp}$ is a surface temperature determined from the sensing 3002 in FIG. 3000 or 3102 in FIG. 31.

where $T_{ntc}$ is an ambient air temperature reading where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.

$f_{ntc}(T_{ntc})$ is a bias in consideration of the temperature sensing mode. For example $f_{axillary}(T_{axillary})=0.2°$ C., $f_{oral}(T_{oral})=0.4°$ C., $f_{rectal}(T_{rectal})=0.5°$ C. and $f_{core}(T_{core})=0.3°$ C.

FIG. 32 is a flowchart of a method of determining correlated temperature of a carotid artery, according to an implementation;

Method 3200 includes determining a correlated body temperature of carotid artery by biasing a sensed temperature of a carotid artery, at block 3202. In one example, the sensed temperature is biased by +0.5° C. to yield the correlated body temperature. In another example, the sensed temperature is biased by −0.5° C. to yield the correlated body temperature. Method 3200 in FIG. 31 is one example of block 3004 in FIG. 30 and block 3104 in FIG. 31. An example of correlating body temperature of a carotid artery follows:

$f_{ntc}(T_{ntc})=0.2°$ C. when $T_{ntc}=26.2°$ C. as retrieved from a data table for body sensing mode.

assumption: $T_{surface\ temp}=37.8°$ C.

$T_{surface\ temp}+f_{ntc}(T_{ntc})=37.8°$ C.$+0.2°$ C.$=38.0°$ C.

$f_{stb}(T_{surface\ temp}+f_{ntc}(T_{ntc}))=38°$ C.$+1.4°$ C.$=39.4°$ C.

assumption: $F4_{body}=0.5°$ C.

$T_{body}=|f_{stb}(T_{surface\ temp}+f_{ntc}(T_{ntc}))+F4_{body}|=|39.4°$ C.$+0.5$ C$|=39.9°$ C.

The correlated temperature for the carotid artery is 39.9° C.

Figure 33:
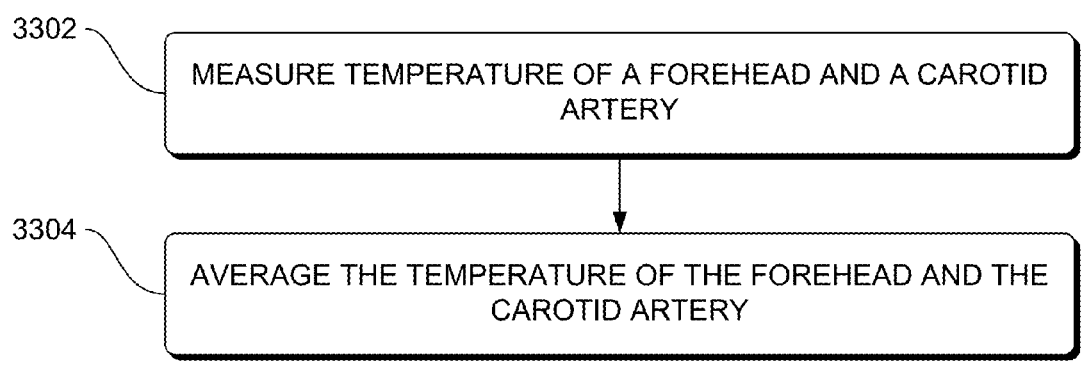
FIG. 33 is a flowchart of a method of forehead and carotid artery sensing, according to an implementation.

FIG. 33 is a flowchart of a method 3300 of forehead and carotid artery sensing, according to an implementation.

Method 3300 includes measuring temperature of a forehead and a carotid artery, at block 3302. Method 3000 in FIG. 30 is one example of block 3302. In an example of correlating temperature of a plurality of external locations, such as a forehead and a carotid artery to an axillary temperature, first a forehead temperature is calculated using formula 1 as follows:

$f_{ntc}(T_{ntc})=0.2°$ C. when $T_{ntc}=26.2°$ C. as retrieved from a data table for axillary sensing mode.

assumption: $T_{surface\ temp}=37.8°$ C.

$T_{surface\ temp}+f_{ntc}(T_{ntc})=37.8°$ C.$+0.2°$ C.$=38.0°$ C.

$f_{stb}(T_{surface\ temp}+f_{ntc}(T_{ntc}))=38°$ C.$+1.4°$ C.$=39.4°$ C.

assumption: $F4_{body}=0°$ C.

$T_{body}=|f_{stb}(T_{surface\ temp}+f_{ntc}(T_{ntc}))+F4_{body}|=|39.4°$ C.$+0$ C$|=39.4°$ C.

And second, a carotid temperature is calculated using formula 1 as follows:

$f_{ntc}(T_{ntc})=0.6°$ C. when $T_{ntc}=26.4°$ C. as retrieved from a data table.

assumption: $T_{surface\ temp}=38.0°$ C.

$T_{surface\ temp}+f_{ntc}(T_{ntc})=38.0°$ C.$+0.6°$ C.$=38.6°$ C.

$f_{stb}(T_{surface\ temp}+f_{ntc}(T_{ntc}))=38.6°$ C.$+1.4$ C$=40.0°$ C.

assumption: $F4_{body}=0°$ C.

$T_{body}=|f_{stb}(T_{surface\ temp}+f_{ntc}(T_{ntc}))+F4_{body}|=|40.0°$ C.$+0$ C$|=40.0°$ C.

Thereafter the correlated temperature for the forehead (39.4° C.) and the correlated temperature for the carotid artery (40.0° C.) are averaged, at block 3304, yielding the final result of the scan of the forehead and the carotid artery as 39.7° C.

Figure 34:
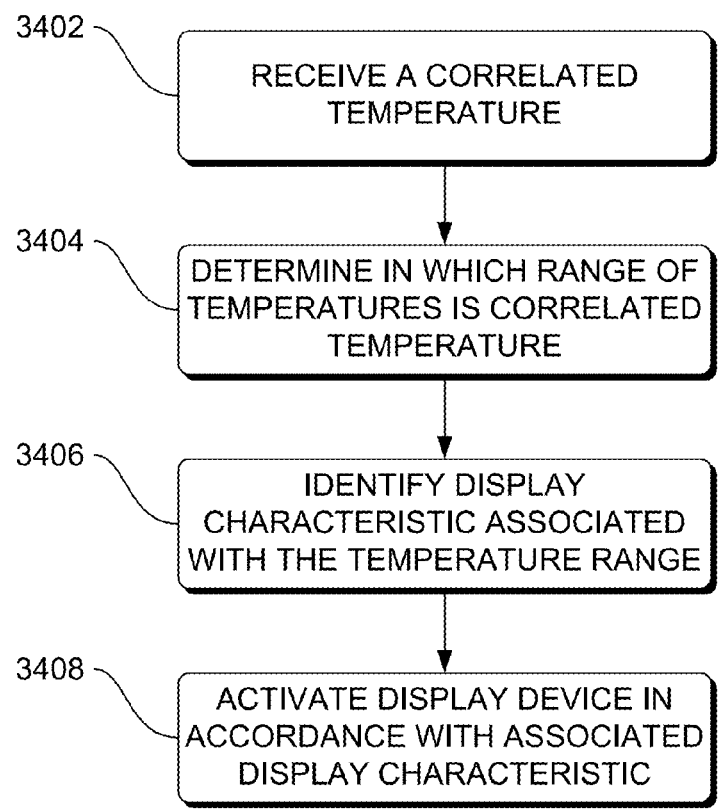
FIG. 34 is a flowchart of a method to display temperature color indicators, according to an implementation.

FIG. 34 is a flowchart of a method 3400 to display temperature color indicators, according to an implementation. Method 3400 provides color rendering in the display device 104 to indicate a general range of a correlated temperature.

Method 3400 includes receiving a correlated temperature, at block 3402. The correlated temperature can be received from the non-contact sensor 110 or the contact sensor 304, or the correlated temperature can be received from a printed circuit board that has adjusted a temperature in reference to either the site on the human or animal of the temperature sensing and or the ambient temperature detected in the vicinity of the apparatus performing the method 3400.

Method 3400 also includes determining in which of a plurality of ranges is the correlated temperature, at block 3404.

Method 3400 also includes identifying a display characteristic that is associated with the determined temperature range, at block 3406. In some implementations, the display characteristic is a color of text. In some implementations, the display characteristic is an image such as a commercial advertisement image.

Method 3400 also includes activating the display device 104 in accordance with the identified display characteristic, at block 3408. In the implementations in which the display characteristic is a color of text, method 3400 provides color rendering in the display device 104 to indicate the general range of the sensed temperature. The medical significance of the temperature is indicated by the displayed color. In the implementations in which the display characteristic is an image such as a commercial advertisement image, method 3400 provides advertising that is relevant to the medical condition of a patient.

In one implementation of a method to display temperature color indicators, according to an implementation of two colors, the method includes the non-contact sensor (such as 110 in FIG. 1) yielding a sensed temperature that is correlated and color changes of the display device (such as 104 in FIG. 1) are related to the correlated temperature, and the display device activates pixels in at least two colors, the colors being in accordance with the correlated temperature.

Figure 35:
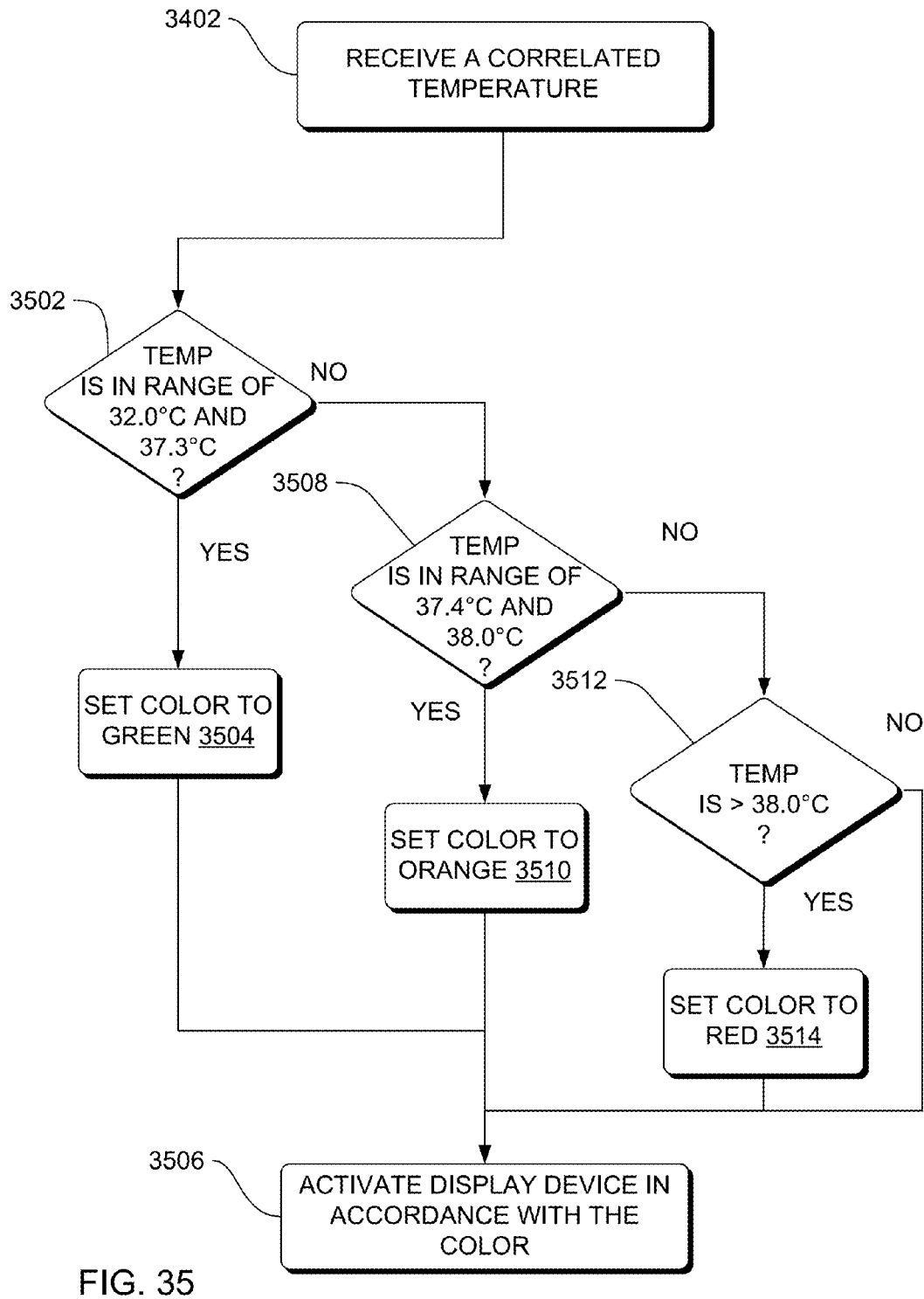
FIG. 35 is a flowchart of a method to display temperature color indicators, according to an implementation of three colors.

FIG. 35 is a flowchart of a method 3500 to display temperature color indicators, according to an implementation of three colors. Method 3500 provides color rendering in the display device 104 to indicate a general range of a correlated temperature.

Method 3500 includes receiving a correlated temperature, at block 1602. The correlated temperature can be received from the non-contact sensor 110 or the contact sensor 512, or the correlated temperature can be received from a printed circuit board that has adjusted a temperature in reference to either the site on the human or animal of the temperature sensing and or the ambient temperature detected in the vicinity of the apparatus performing the method 3500.

Method 3500 also includes determining whether or not the correlated temperature is in the range of 32.0° C. and 37.3° C., at block 3502. If the correlated temperature is in the range of 32.0° C. and 37.3° C., then the color is set to 'green' to indicate a temperature of no medical concern, at block 3504 and the background of the display device 104 is activated in accordance with the color, at block 3506.

If the correlated temperature is not the range of 32.0° C. and 37.3° C., then method 3500 also includes determining whether or not the correlated temperature is in the range of 37.4° C. and 38.0° C., at block 3508. If the sensed temperature is in the range of 37.4° C. and 38.0° C., then the color is set to 'orange' to indicate caution, at block 3510 and the background of the display device 104 is activated in accordance with the color, at block 3506.

If the correlated temperature is not the range of 37.4° C. and 38.0° C., then method 3500 also includes determining whether or not the correlated temperature is over 38.0° C., at block 3512. If the correlated temperature is over 38.0° C., then the color is set to 'red' to indicate alert, at block 3512 and the background of the display device 104 is activated in accordance with the color, at block 3506.

Method 3500 assumes that temperature is correlated in gradients of 10ths of a degree. Other temperature range boundaries are used in accordance with other gradients of temperature sensing.

In some implementations, some pixels in the display device 104 are activated as a green color when the correlated temperature is between 36.3° C. and 37.3° C. (97.3° F. to 99.1° F.), some pixels in the display device 104 are activated as an orange color when the correlated temperature is between 37.4° C. and 37.9° C. (99.3° F. to 100.2° F.), some pixels in the display device 104 are activated as a red color when the correlated temperature is greater than 38° C. (100.4° F.). In some implementations, the display device 104 is a backlit LCD screen (which is easy to read in a dark room) and some pixels in the display device 104 are activated (remain lit) for about 5 seconds after the button 106 is released. After the display device 104 has shut off, another temperature reading can be taken by the apparatus. The color change of the display device 104 is to alert the user of the apparatus of a potential increase of body temperature of the human or animal subject. Temperature reported on the display can be used for treatment decisions.

Figure 36:
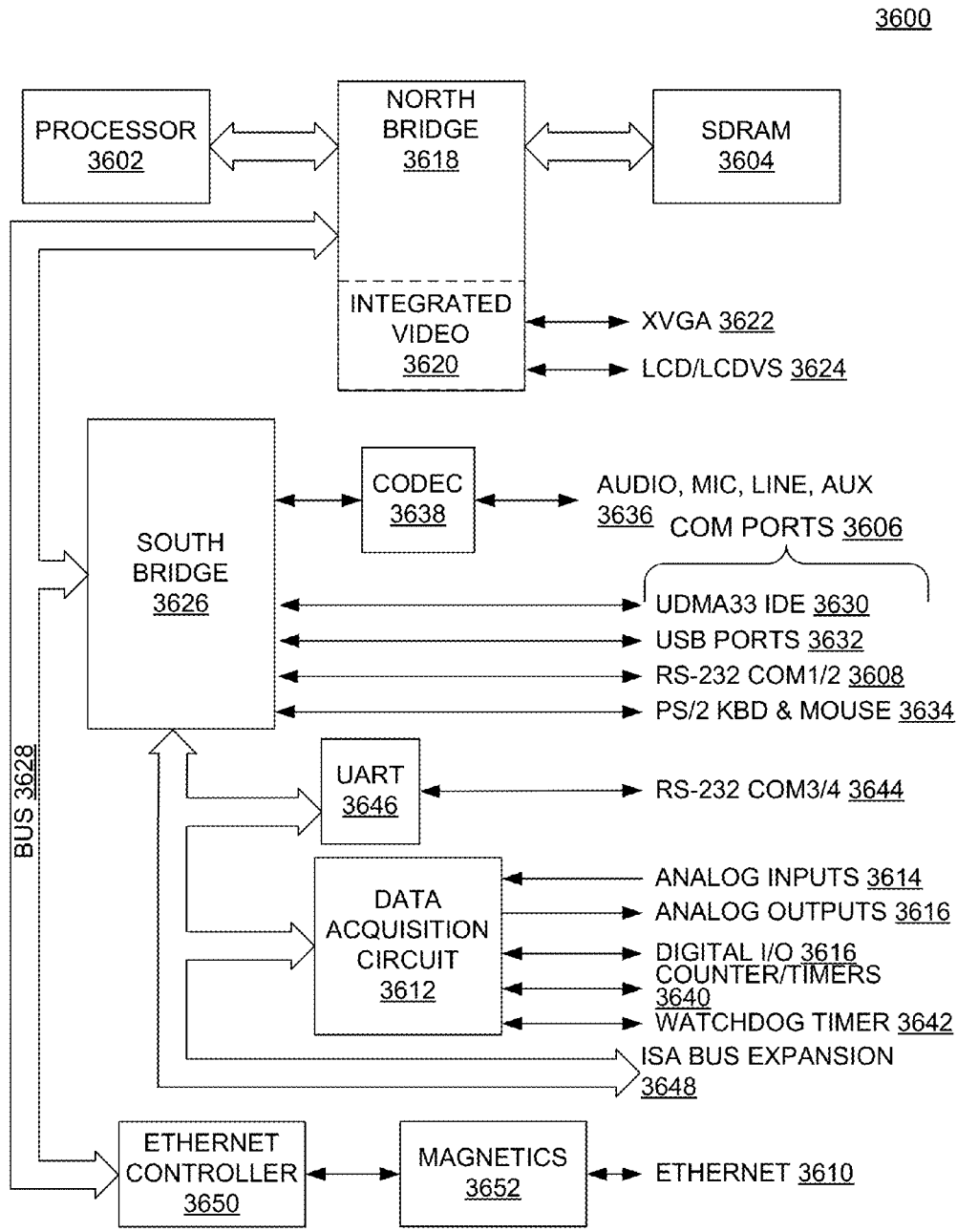
FIG. 36 is a block diagram of a thermometer control computer, according to an implementation.

In some implementations, methods 3000-3500 are implemented as a sequence of instructions which, when executed by a processor 3602 in FIG. 36, cause the processor to perform the respective method. In other implementations, methods 3000-3500 are implemented as a computer-accessible medium having executable instructions capable of directing a processor, such as processor 3602 in FIG. 36, to perform the respective method. In varying implementations, the medium is a magnetic medium, an electronic medium, or an optical medium.

Hardware and Operating Environment

FIG. 36 is a block diagram of a thermometer control computer 3600, according to an implementation. The thermometer control computer 3600 includes a processor (such as a Pentium III processor from Intel Corp. in this example) which includes dynamic and static ram and non-volatile program read-only-memory (not shown), operating memory 3604 (SDRAM in this example), communication ports 3606 (e.g., RS-232 3608 COM1/2 or Ethernet 3610), and a data acquisition circuit 3612 with analog inputs 3614 and analog outputs 3616.

In some implementations of the thermometer control computer 3600, the data acquisition circuit 3612 is also coupled to counter timer ports 3640 and watchdog timer ports 3642. In some implementations of the thermometer control computer 3600, an RS-232 port 3644 is coupled through a universal asynchronous receiver/transmitter (UART) 3646 to a bridge 3626.

In some implementations of the thermometer control computer 3600, the Ethernet port 3610 is coupled to the bus 3628 through an Ethernet controller 3650.

With proper digital amplifiers and analog signal conditioners, the thermometer control computer 3600 can be programmed to drive the display device 602. The sensed temperatures can be received by non-contact sensors 110 and 304, the output of which, after passing through appropriate signal conditioners, can be read by the analog to digital converters that are part of the data acquisition circuit 3612. Thus the temperatures can be made adjusted for ambient temperature or the physical site of the human or animal that was examined for temperature on in as part of its decision-making software that acts to process and display sensed temperature.

Figure 37:
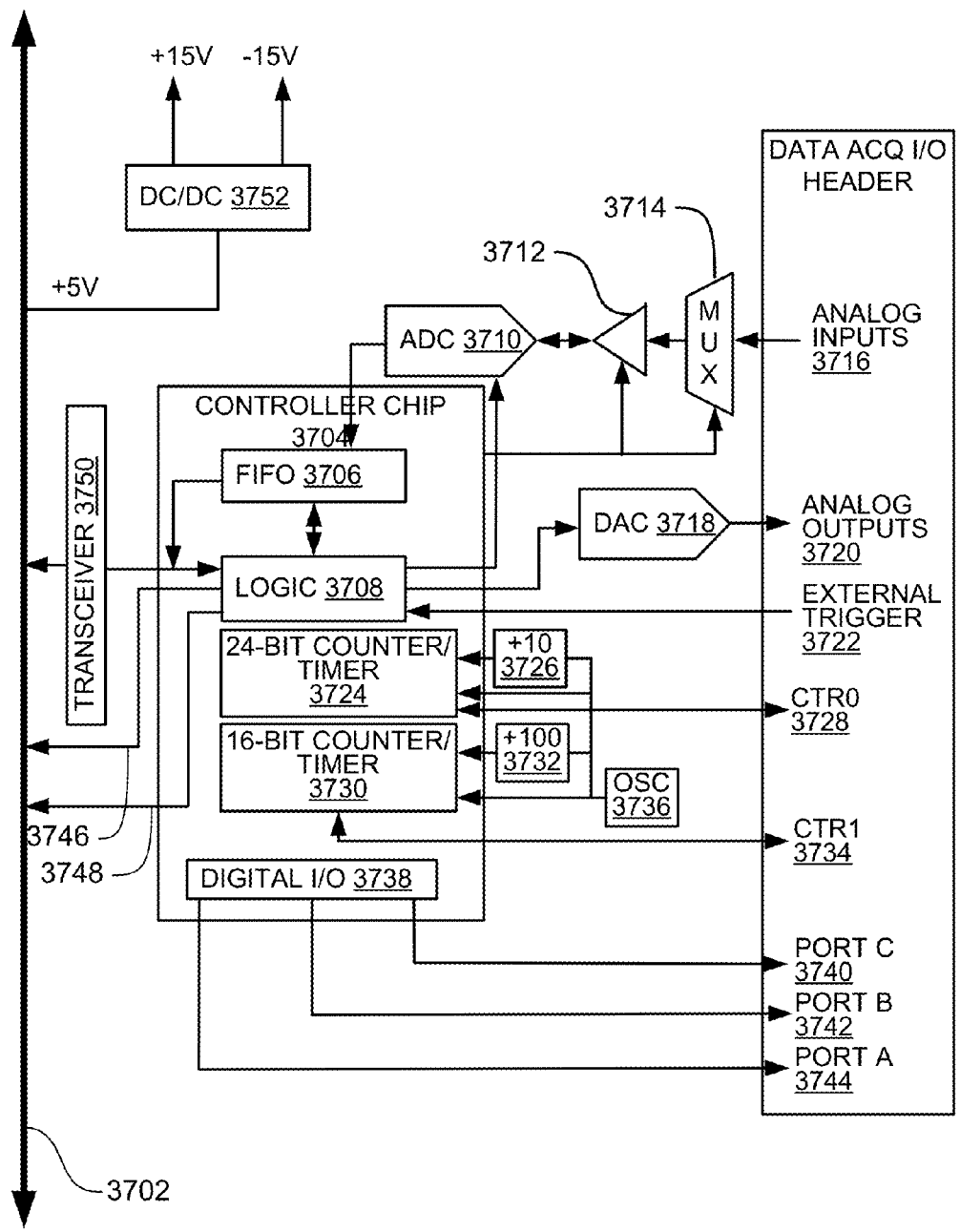
FIG. 37 is a block diagram of a data acquisition circuit of a thermometer control computer, according to an implementation.

FIG. 37 is a block diagram of a data acquisition circuit 3700 of a thermometer control computer, according to an implementation. The data acquisition circuit 3700 is one example of the data acquisition circuit 3612 in FIG. 36 above. Some implementations of the data acquisition circuit 3700 provide 16-bit A/D performance with input voltage capability up to +/−10V, and programmable input ranges.

The data acquisition circuit 3700 can include a bus 3702, such as a conventional PC/104 bus. The data acquisition circuit 3700 can be operably coupled to a controller chip 3704. Some implementations of the controller chip 3704 include an analog/digital first-in/first-out (FIFO) buffer 3706 that is operably coupled to controller logic 3708. In some implementations of the data acquisition circuit 3700, the FIFO buffer 3706 receives signal data from and analog/digital converter (ADC) 3710, which exchanges signal data with a programmable gain amplifier 3712, which receives data from a multiplexer 3714, which receives signal data from analog inputs 3716.

In some implementations of the data acquisition circuit 3700, the controller logic 3708 sends signal data to the ADC 3710 and a digital/analog converter (DAC) 3718. The DAC 3718 sends signal data to analog outputs. The analog outputs, after proper amplification, can be used to modulate coolant valve actuator positions. In some implementations of the data acquisition circuit 3700, the controller logic 3708 receives signal data from an external trigger 3722.

In some implementations of the data acquisition circuit 3700, the controller chip 3704 includes a digital input/output (I/O) component 3738 that sends digital signal data to computer output ports.

In some implementations of the data acquisition circuit 3700, the controller logic 3708 sends signal data to the bus 3702 via a control line 3746 and an interrupt line 3748. In some implementations of the data acquisition circuit 3700, the controller logic 3708 exchanges signal data to the bus 3702 via a transceiver 3750.

Some implementations of the data acquisition circuit 3700 include 12-bit D/A channels, programmable digital I/O lines, and programmable counter/timers. Analog circuitry can be placed away from the high-speed digital logic to ensure low-noise performance for important applications. Some implementations of the data acquisition circuit 3700 are fully supported by operating systems that can include, but are not limited to, DOS™, Linux™, RTLinux™, QNX™, Windows 98/NT/2000/XP/CE™, Forth™, and VxWorks™ to simplify application development.

CONCLUSION

A non-contact thermometer that senses temperature of a plurality of external locations is described. A technical effect of the non-contact thermometer is visual display of a temperature that is correlated from the plurality of external locations. Another technical effect of the non-contact thermometer is visual display of a temperature that is correlated from a carotid source point. Although specific implementations are illustrated and described herein, it will be appreciated by those of ordinary skill in the art that any arrangement which is calculated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future non-contact temperature sensing devices, different temperature measuring sites on humans or animals and new display devices.

The terminology used in this application meant to include all temperature sensors, processors and user environments and alternate technologies which provide the same functionality as described herein.

The invention claimed is:

1. An apparatus to determine a body temperature from a carotid artery source point, the apparatus comprising:
    a housing;
    a non-contact electromagnetic sensor operably mounted to the housing, the non-contact electromagnetic sensor being operable to receive electromagnetic energy from the carotid artery source point of a subject and operable to generate a numerical representation of the electromagnetic energy of the carotid artery source point;
    a printed circuit board mounted in the housing, electrically coupled to the non-contact electromagnetic sensor and operable to determine the body temperature of the subject from the numerical representation of the electromagnetic energy of the carotid artery source point,
    wherein determining the body temperature of the subject further comprises:
        calculating the body temperature as $f_{stb}(T_{surface\ temp} + f_{ntc}(T_{ntc})) + F4_{body}$,
        where $f_{stb}$ is a representation of a surface of the body,
        where $T_{surface\ temp}$ is the numerical representation of the electromagnetic energy of the carotid source point,
        where $f_{ntc}$ is mathematical formula of an ambient temperature reading,
        where $T_{ntc}$ is the ambient air temperature reading,
        where $F4_{body}$ is the representation of the calibration difference,
        $f_{ntc}(T_{ntc})$ is the bias in consideration of the temperature sensing mode; and
    a button operably coupled to the printed circuit board.

2. The apparatus of claim 1, wherein the carotid artery source point further comprises:
    not more than one carotid artery source point.

3. The apparatus of claim 1, wherein the bias further comprises:
    +0.5° C.

4. The apparatus of claim 1, wherein the body temperature of the subject further comprises:
    a core temperature of the subject.

5. The apparatus of claim 1, wherein the body temperature of the subject further comprises:
    an axillary temperature of the subject.

6. The apparatus of claim 1, wherein the body temperature of the subject further comprises:
    a rectal temperature of the subject.

7. The apparatus of claim 1, wherein the body temperature of the subject further comprises:
    an oral temperature of the subject.

8. The apparatus of claim 1, wherein the printed circuit board further comprises:
    a microprocessor.

9. The apparatus of claim 1, wherein the body temperature of the subject further comprises:

a core temperature of the subject, an axillary temperature of the subject, a rectal temperature of the subject and an oral temperature of the subject.

10. An apparatus to measure a body temperature, the apparatus comprising:
   a housing;
   a non-contact sensor operably mounted to the housing, the non-contact sensor having an electromagnetic sensor, the electromagnetic sensor being operable to:
      receive electromagnetic energy from a plurality of body source points of a subject including a carotid source point of the subject; and
      generate a numerical representation of the electromagnetic energy of each of the plurality of body source points;
   a printed circuit board mounted in the housing and operable to determine the body temperature of the subject from the numerical representation of the electromagnetic energy of each of the plurality of body source points, wherein determining the body temperature of the subject further comprises:
      calculating the body temperature, yielding a calculated body temperature of each of the plurality of source points; and
      averaging the calculated body temperature of each of the plurality of source points, yielding the body temperature,
   wherein calculating the body temperature further comprises:
      calculating the body temperature as $f_{stb}(T_{surface\ temp} + f_{ntc}(T_{ntc})) + F4_{body}$,
      where $f_{stb}$ is a representation of a surface of the body,
      where $T_{surface\ temp}$ is the numerical representation of the electromagnetic energy of the carotid source point,
      where $f_{ntc}$ is mathematical formula of an ambient temperature reading,
      where $T_{ntc}$ is the ambient air temperature reading,
      where $F4_{body}$ is the representation of the calibration difference,
      $f_{ntc}(T_{ntc})$ is the bias in consideration of the temperature sensing mode; and
   a display device operably coupled to the printed circuit board and operable to display the body temperature.

11. The apparatus of claim 10, wherein the plurality of body source points further comprises:
   not more than two body source points.

12. The apparatus of claim 11, wherein the two body source points further comprise:
   the carotid source point; and
   a forehead source point.

13. The apparatus of claim 10, wherein the plurality of body source points further comprises:
   the carotid source point; and
   a forehead source point.

14. The apparatus of claim 10, wherein the printed circuit board further comprises:
   a microprocessor.

15. The apparatus of claim 10, wherein the electromagnetic sensor further comprises:
   an infrared temperature sensor.

16. The apparatus of claim 10, wherein the temperature of the subject further comprises:
   the temperature of the subject selected from a group of temperatures of the subject consisting of a core temperature of the subject, an axillary temperature of the subject, a rectal temperature of the subject and an oral temperature of the subject.

17. A method to measure body temperature, the method comprising:
   sensing electromagnetic energy at a plurality of external source points on a subject, yielding a sensed electromagnetic energy of the plurality of external source points;
   determining the body temperature of the subject from the sensed electromagnetic energy of the plurality of external source points including a carotid source point, the determining being performed by a microprocessor, wherein determining the body temperature of the subject further comprises:
      calculating the body temperature as $f_{stb}(T_{surface\ temp} + f_{ntc}(T_{ntc})) + F4_{body}$,
      where $f_{stb}$ is a representation of a surface of the body,
      where $T_{surface\ temp}$ is the numerical representation of the electromagnetic energy of the carotid source point,
      where $f_{ntc}$ is mathematical formula of an ambient temperature reading,
      where $T_{ntc}$ is the ambient air temperature reading,
      where $F4_{body}$ is the representation of the calibration difference,
      $f_{ntc}(T_{ntc})$ is the bias in consideration of the temperature sensing mode; and
   averaging the body temperature of each of the plurality of external source points, yielding the body temperature.

18. The method of claim 17, wherein the temperature of the subject consists of:
   a core temperature of the subject, an axillary temperature of the subject, a rectal temperature of the subject and an oral temperature of the subject.

19. The method of claim 17, wherein the sensing further comprises:
   sensing the electromagnetic energy at the carotid source point on the subject and a forehead source point on the subject, yielding the sensed electromagnetic energy of the plurality of external source points.

* * * * *